(12) United States Patent
Shirley et al.

(10) Patent No.: US 8,333,958 B2
(45) Date of Patent: *Dec. 18, 2012

(54) HSA-FREE FORMULATIONS OF INTERFERON-BETA

(75) Inventors: Bret A Shirley, Waltham, MA (US);
Susan Babuka, Oakland, CA (US);
Bao-Lu Chen, San Ramon, CA (US);
Maninder Hora, Danville, CA (US);
Minna Choe, Danville, CA (US);
Melanie Tellers, Cranford, NJ (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/004,658

(22) Filed: Jan. 11, 2011

(65) Prior Publication Data

US 2011/0104116 A1    May 5, 2011

Related U.S. Application Data

(63) Continuation of application No. 12/082,177, filed on Apr. 9, 2008, now Pat. No. 7,892,531, which is a continuation of application No. 11/062,146, filed on Feb. 18, 2005, now Pat. No. 7,371,373, which is a continuation of application No. 10/821,333, filed on Apr. 9, 2004, now Pat. No. 7,399,463, which is a continuation of application No. 10/035,397, filed on Oct. 25, 2001, now Pat. No. 6,887,462.

(60) Provisional application No. 60/330,404, filed on Oct. 18, 2001, provisional application No. 60/282,614, filed on Apr. 9, 2001.

(51) Int. Cl.
*A61K 45/00* (2006.01)
*C07K 17/00* (2006.01)

(52) U.S. Cl. ...... 424/85.6; 424/85.1; 530/351; 514/17.9

(58) Field of Classification Search .................. None
See application file for complete search history.

(56) References Cited

U.S. PATENT DOCUMENTS

| | | |
|---|---|---|
| 4,439,181 A | 3/1984 | Blackshear et al. |
| 4,462,940 A | 7/1984 | Hanisch et al. |
| 4,465,622 A | 8/1984 | Nobuhara et al. |
| 4,588,585 A | 5/1986 | Mark et al. |
| 4,605,555 A | 8/1986 | Sato et al. |
| 4,605,556 A | 8/1986 | Sato et al. |
| 4,647,454 A | 3/1987 | Cymbalista |
| 4,675,184 A | 6/1987 | Hasegawa et al. |
| 5,004,605 A | 4/1991 | Hershenson et al. |
| 5,104,651 A | 4/1992 | Boone et al. |
| 5,151,265 A | 9/1992 | Hwang-Felgner et al. |
| 5,183,746 A | 2/1993 | Shaked et al. |
| 5,609,868 A | 3/1997 | Lowther et al. |
| 5,643,566 A | 7/1997 | Hanisch et al. |
| 5,762,923 A | 6/1998 | Gross et al. |
| 5,763,409 A | 6/1998 | Bayol et al. |
| 6,465,425 B1 | 10/2002 | Tracy et al. |
| 6,525,102 B1 | 2/2003 | Chen et al. |
| 2003/0118548 A1 | 6/2003 | McCaman et al. |

FOREIGN PATENT DOCUMENTS

| | | |
|---|---|---|
| CA | 2304808 | 9/1997 |
| EP | 0 080 879 | 10/1986 |
| EP | 0 284 249 | 9/1988 |
| EP | 0 164 397 | 7/1990 |
| EP | 0 410 207 | 1/1991 |
| EP | 0 133 767 | 4/1991 |
| EP | 0 477 386 | 1/1992 |
| EP | 0 215 658 | 6/1994 |
| EP | 0 736 303 | 10/1996 |
| EP | 0 759 775 | 3/1997 |
| WO | WO 89/02750 | 4/1989 |
| WO | WO 89/05158 | 6/1989 |
| WO | WO 90/06762 | 6/1990 |
| WO | WO 91/16038 | 10/1991 |
| WO | WO 95/31213 | 11/1995 |
| WO | WO 95/31479 | 11/1995 |
| WO | WO 98/28007 | 7/1998 |
| WO | WO 99/15193 | 4/1999 |
| WO | WO 99/51272 | 10/1999 |

OTHER PUBLICATIONS

Nieforth et al., Clin Pharmacol Ther. 1996 59: 636-46.*
Arnason, Clinical Immunology and Immunopathology, 1996; 81: 1-11.*
Boublik et al., "Conformation and Activity of Recombinant Human Fibroblast Interferon-B," Journal of Inerferon Research, 1990, pp. 213-219, vol. 10.
Utsumi et al., "Stability of Human Interferon-Beta1: Oligomeric human Interferon-Beta1 Is Inactive but is Reactivated by Monomerization," Biochimica et Biophysica Acta, 1989, pp. 167-172, vol. 998.
Merck Index, 1989, p. 859.

* cited by examiner

*Primary Examiner* — Bridget E Bunner
*Assistant Examiner* — Christina Borgeest

(57) ABSTRACT

Stabilized pharmaceutical compositions comprising substantially monomeric interferon-beta (IFN-β) and methods useful in their preparation are provided. The compositions comprise the IFN-β solubilized in a low-ionic-strength formulation that maintains the composition at a pH of about 3.0 to about 5.0. Methods for preparing these compositions, and for increasing solubility of IFN-β in pharmaceutical compositions, are provided.

43 Claims, 23 Drawing Sheets

SEQUENCE LISTING

<160> NUMBER OF SEQ ID NOS: 2

<210> SEQ ID NO 1
<211> LENGTH: 166
<212> TYPE: PRT
<213> ORGANISM: Homo sapiens

<400> SEQUENCE: 1

Met Ser Tyr Asn Leu Leu Gly Phe Leu Gln Arg Ser Ser Asn Phe Gln

```
                1               5                  10                 15
Cys Gln Lys Leu Leu Trp Gln Leu Asn Gly Arg Leu Glu Tyr Cys Leu
            20                  25                 30

Lys Asp Arg Met Asn Phe Asp Ile Pro Glu Glu Ile Lys Gln Leu Gln
            35                  40                 45

Gln Phe Gln Lys Glu Asp Ala Ala Leu Thr Ile Tyr Glu Met Leu Gln
    50                  55                 60

Asn Ile Phe Ala Ile Phe Arg Gln Asp Ser Ser Thr Gly Trp Asn
65                  70                  75                 80

Glu Thr Ile Val Glu Asn Leu Leu Ala Asn Val Tyr His Gln Ile Asn
                85                  90                 95

His Leu Lys Thr Val Leu Glu Glu Lys Leu Glu Lys Glu Asp Phe Thr
                100                 105                110

Arg Gly Lys Leu Met Ser Ser Leu His Leu Lys Arg Tyr Tyr Gly Arg
            115                 120                125

Ile Leu His Tyr Leu Lys Ala Lys Glu Tyr Ser His Cys Ala Trp Thr
            130                 135                140

Ile Val Arg Val Glu Ile Leu Arg Asn Phe Tyr Phe Ile Asn Arg Leu
145                 150                 155                160

Thr Gly Tyr Leu Arg Asn
            165
```

<210> SEQ ID NO 2
<211> LENGTH: 166
<212> TYPE: PRT
<213> ORGANISM: Artificial Sequence
<220> FEATURE:
<223> OTHER INFORMATION: Human interferon-beta mutein with cysteine to
      serine substitution at position 17

<400> SEQUENCE: 2

```
Met Ser Tyr Asn Leu Leu Gly Phe Leu Gln Arg Ser Ser Asn Phe Gln
1               5                   10                 15

Ser Gln Lys Leu Leu Trp Gln Leu Asn Gly Arg Leu Glu Tyr Cys Leu
            20                  25                 30

Lys Asp Arg Met Asn Phe Asp Ile Pro Glu Glu Ile Lys Gln Leu Gln
            35                  40                 45

Gln Phe Gln Lys Glu Asp Ala Ala Leu Thr Ile Tyr Glu Met Leu Gln
    50                  55                 60

Asn Ile Phe Ala Ile Phe Arg Gln Asp Ser Ser Thr Gly Trp Asn
65                  70                  75                 80

Glu Thr Ile Val Glu Asn Leu Leu Ala Asn Val Tyr His Gln Ile Asn
                85                  90                 95

His Leu Lys Thr Val Leu Glu Glu Lys Leu Glu Lys Glu Asp Phe Thr
                100                 105                110

Arg Gly Lys Leu Met Ser Ser Leu His Leu Lys Arg Tyr Tyr Gly Arg
            115                 120                125

Ile Leu His Tyr Leu Lys Ala Lys Glu Tyr Ser His Cys Ala Trp Thr
            130                 135                140

Ile Val Arg Val Glu Ile Leu Arg Asn Phe Tyr Phe Ile Asn Arg Leu
145                 150                 155                160

Thr Gly Tyr Leu Arg Asn
            165
```

HSA-FREE FORMULATIONS OF INTERFERON-BETA

CROSS-REFERENCE TO RELATED APPLICATION

This application is a continuation of application Ser. No. 12/082,177, filed Apr. 9, 2008, now U.S. Pat. No. 7,892,531, which is a continuation of application Ser. No. 11/062,146, filed on Feb. 18, 2005, now U.S. Pat. No. 7,371,373, which is a continuation of application Ser. No. 10/821,333, filed on Apr. 9, 2004 now U.S. Pat. No. 7,399,463, which is a continuation of Ser. No. 10/035,397, filed on Oct. 25, 2001, now U.S. Pat. No. 6,887,462, which claims benefit of U.S. Application No. 60/330,404 filed on Oct. 18, 2001 and U.S. Application 60/282,614 filed on Apr. 9, 2001, the entire disclosures of which are hereby incorporated by reference.

FIELD OF THE INVENTION

The invention relates generally to pharmaceutical compositions, more particularly to stabilized formulations of interferon-n that are free of human serum albumin as an added pharmaceutical excipient.

BACKGROUND OF THE INVENTION

The interferons are a family of glycoproteins whose secretion from cells is induced by a number of signals including viruses, double-stranded RNAs, other polynucleotides, antigens, and mitogens. Interferons exhibit multiple biological activities, including antiviral, antiproliferative, and immunomodulatory activities. At least three distinct types of human interferons, α, β, and γ, have been distinguished based on a number of factors, including anti-viral and anti-proliferative activities.

Interferon-β (IFN-β) is the first identified effective treatment for those with multiple sclerosis (MS), and has been demonstrated to reduce the number of attacks suffered by patients with relapsing and remitting MS, and secondary progressive MS. IFN-β compositions are also useful in the treatment of hepatitis B and C infections.

As with all protein-based pharmaceuticals, one major obstacle that must be overcome in the use of IFN-β as a therapeutic agent is the loss of pharmaceutical utility that can result from its instability in pharmaceutical formulations. Physical instabilities that threaten polypeptide activity and efficacy in pharmaceutical formulations include denaturation and formation of soluble and insoluble aggregates, while chemical instabilities include hydrolysis, imide formation, oxidation, racemization, and deamidation. Some of these changes are known to lead to the loss or reduction of the pharmaceutical activity of the protein of interest. In other cases, the precise effects of these changes are unknown, but the resulting degradative products are still considered to be pharmaceutically unacceptable due to the potential for undesirable side effects.

The stabilization of polypeptides in pharmaceutical compositions remains an area in which trial and error plays a major role (reviewed by Wang (1999) *Int. J. Pharm.* 185:129-188; Wang and Hanson (1988) *J. Parenteral Sci. Tech.* 42:S3-S26). Excipients that are added to polypeptide pharmaceutical formulations to increase their stability include buffers, sugars, surfactants, amino acids, polyethylene glycols, and polymers, but the stabilizing effects of these chemical additives vary depending on the protein.

One of the major obstacles to preparing stabilized IFN-β pharmaceutical formulations has been the poor solubility of the IFN-β molecule. Current formulations employ the use of HSA as a solubility-enhancing agent for IFN-β. However, the use of HSA has drawbacks. HSA is a product of human blood and must therefore be harvested from human subjects. While steps are taken to reduce the risk, the use of human blood products such as HSA carries with it the potential introduction of human viruses such as HIV and HCV. The introduction of HSA into the formulation also interferes with the ability to properly determine the stability of IFN-β in the formulation. This is because HSA and IFN-β are both proteins, and the HSA interferes with some of the IFN-β stability-indicating assays.

Furthermore, IFN-β is a protein that exhibits aggregate formation when prepared in pharmaceutical compositions, and hence the amount of this protein in its monomeric biologically active state is compromised during storage of these compositions. Aggregate formation by a polypeptide such as IFN-β during storage of a pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the IFN-β pharmaceutical composition is administered using an infusion system. In addition, injection of a pharmaceutical composition comprising the aggregated form of a protein has the potential for generating an immunogenic reaction to the aggregated protein.

Consequently, there is a need for additional IFN-β pharmaceutical compositions comprising physiologically compatible stabilizers that improve the solubility of this protein and stabilize the protein against aggregate formation, thereby enhancing their pharmaceutical utility.

SUMMARY OF THE INVENTION

Compositions comprising interferon-beta (IFN-β) as a therapeutically active component and methods useful in their preparation are provided. The compositions are stabilized pharmaceutical compositions that are free of human serum albumin (HSA) as a pharmaceutical excipient and which comprise substantially monomeric IFN-β solubilized in a low-ionic-strength formulation. The low-ionic-strength formulation is a solution that comprises a buffer in an amount sufficient to maintain the composition at a specified pH plus or minus 0.5 units, where the specified pH is about 3.0 to about 5.0, and which has an ionic strength of not greater than about 60 mM. A non-ionic tonicifying agent is incorporated into the pharmaceutical compositions to render the compositions isotonic, where the tonicifying agent is a carbohydrate. Methods for increasing solubility of IFN-β in pharmaceutical compositions, and for increasing the amount of monomeric IFN-β in these compositions, without the use of human serum albumin are also provided.

DETAILED DESCRIPTION OF THE INVENTION

Figure 1:
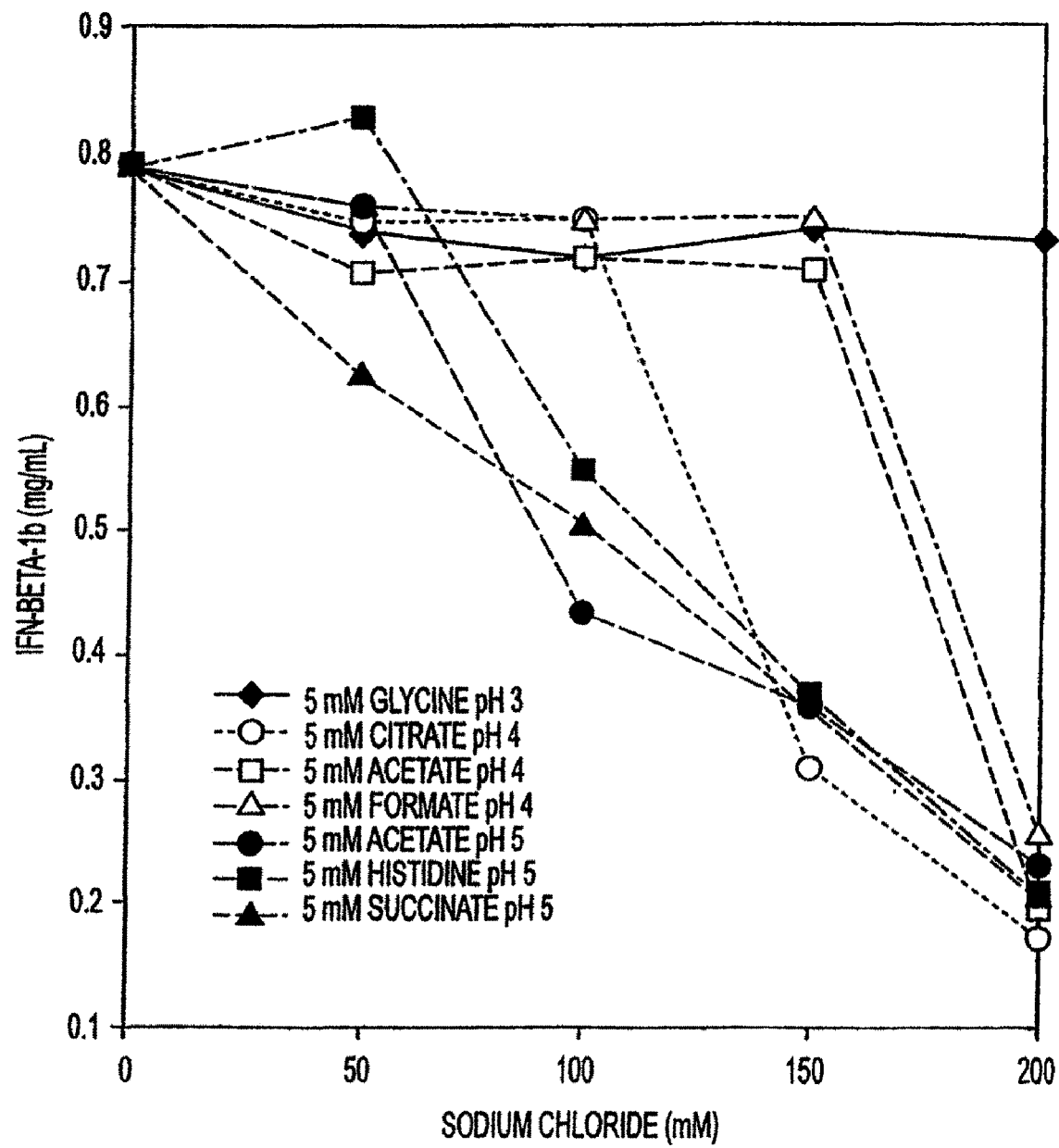
FIG. 1 shows IFN-β-1b solubility in sodium chloride solutions.

The present invention is directed to stabilized pharmaceutical compositions that comprise interferon-beta (IFN-β) and methods for their preparation. These compositions are prepared in the absence of human serum albumin (HSA), and are thus free of this pharmaceutical excipient. Such compositions are referred to herein as "HSA-free" IFN-β pharmaceutical compositions. The compositions comprise substantially monomeric IFN-β that is solubilized in a low-ionic-strength formulation. By "low-ionic-strength" formulation is intended a solution that comprises a buffer in an amount that is sufficient to maintain the pH of the pharmaceutical composition within plus or minus 0.5 units of a specified pH, and which has an ionic strength that is not greater than about 60 mM. By "ionic strength" is intended the standard chemical definition as applied to a solution, where ionic strength of a solution is equal to $\frac{1}{2}\Sigma c_i z_i^2$, in which c is the concentration and z is the charge. The buffer is present in the low-ionic-strength formulation at a concentration of about 1 mM to about 30 mM, preferably about 2 mM to about 25 mM, more preferably about 2 mM to about 20 mM, even more preferably about 2 mM to about 10 mM, still more preferably about 2 mM to about 5 mM. Thus, in some embodiments, the low-ionic-strength formulation comprises a buffer at a concentration of about 2 mM to about 10 mM, about 2 mM to about 7 mM, about 2 mM to about 5 mM, about 2 mM, about 3 mM, about 4 mM, or about 5 mM. Suitable buffers that can be used to prepare the low-ionic-strength formulation in which the IFN-β is solubilized include, but are not limited to, glycine, aspartic acid, sodium succinate, citrate, formate, acetate, glutamic acid, histidine, imidazole, and phosphate, preferably glycine, aspartic acid, and sodium succinate, more preferably glycine and aspartic acid.

Preferably the low-ionic-strength formulation has an ionic strength that is not greater than about 60 mM, more preferably not greater than about 40 mM, still more preferably not greater than about 20 mM. In some embodiments, the ionic strength of the formulation is solely determined by the buffer concentration, and hence the formulation does not have additional ionic species, such as sodium chloride, potassium chloride, magnesium chloride, ammonium salt, and the like, contributing to its ionic strength.

Use of a low-ionic-strength formulation that is a solution comprising a buffer at a concentration of about 1 mM to about 30 mM, preferably at about 2 mM to about 5 mM, provides for the preparation of stabilized IFN-β pharmaceutical compositions that have a pH of about 3.0 to about 5.0, preferably about 3.0 to about 4.5, more preferably about 3.0 to about 4.0, still more preferably about 3.5 to about 4.0, most preferably about 4.0, depending upon the particular buffer used. Thus, when the buffer is glycine, the pH of the composition is about 3.0 to about 3.5, preferably about 3.0. When the buffer is aspartic acid, the pH of the composition is about 3.5 to about 4.5, preferably about 4.0. When the buffer is sodium succinate, the pH of the composition is about 4.5 to about 5.0, preferably about 5.0.

By maintaining the pH of the IFN-β pharmaceutical compositions of the invention within the range of about pH 3.0 to about pH 5.0 it is possible to increase the solubility of IFN-β in these compositions beyond that normally possible in the absence of the use of human serum albumin. Furthermore, by incorporating IFN-β into a low-ionic-strength formulation as defined herein it is possible to prepare pharmaceutical compositions that comprise substantially monomeric IFN-β. By "substantially monomeric" is intended that the majority of IFN-β (by weight) present in the composition is in its monomeric form rather than an aggregated form. By "aggregated" is intended a physical interaction between the polypeptide molecules that results in the formation of multimers (dimers, trimers, etc.) that may remain soluble or that may precipitate out of solution. The monomeric form of the IFN-β polypeptide remains soluble, and hence is said to be "solubilized" in the low-ionic-strength formulation or pharmaceutical compositions of the present invention. The percentage (by weight) of IFN-β that is in its monomeric form in the HSA-free compositions of the invention may vary from 80% or greater. The present invention thus provides HSA-free, IFN-β pharmaceutical compositions that comprise at least about 80% of the IFN-β in its monomeric form, as opposed to its aggregated form, preferably at least about 85%, more preferably at least about 90%, still more preferably at least about 91%, 92%, 93%, 94%, 95%, 96%, 97%, 98%, 99% or more of the IFN-β in its monomeric form.

In some embodiments of the invention, the HSA-free IFN-β pharmaceutical compositions further comprise a non-ionic tonicifying agent in an amount sufficient to render the compositions isotonic with body fluids. The compositions can be made isotonic with a number of non-ionic tonicity modifying agents ordinarily known to those in the art. These are typically carbohydrates of various classifications (see, for example, Voet and Voet (1990) *Biochemistry* (John Wiley & Sons, New York). Monosaccharides classified as aldoses such as glucose, mannose, arabinose, and ribose, as well as those classified as ketoses such as fructose, sorbose, and xylulose can be used as non-ionic tonicifying agents in the present invention. Disaccharides such a sucrose, maltose, trehalose, and lactose can also be used. In addition, alditols (acyclic polyhydroxy alcohols) such as glycerol, mannitol, xylitol, and sorbitol are non-ionic tonicifying agents useful in the present invention. The most preferred non-ionic tonicifying agents are trehalose, sucrose, and mannitol, or a combination thereof. The non-ionic tonicifying agent is added in an amount sufficient to render the formulation isotonic with body fluids. When incorporated into the HSA-free IFN-β pharmaceutical compositions, the non-ionic tonicifying agent is present at a concentration of about 1% to about 10%, depending upon the agent used. Thus, in one embodiment, the non-ionic tonicifying agent is trehalose or sucrose at a concentration of about 8% to about 10%, preferably about 9% by weight per volume, and preferably is trehalose at this concentration. In another embodiment, the non-ionic tonicifying agent is mannitol at a concentration of about 4% to about 6%, preferably about 5% by weight per volume. In other embodiments, the non-ionic tonicifying agent is a combination of trehalose and mannitol, or sucrose and mannitol, where the trehalose and sucrose are present at a concentration of about 1% by weight per volume and the mannitol is present at a concentration of about 3% to about 5% by weight per volume, preferably about 4.6% by weight per volume.

The HSA-free IFN-β pharmaceutical compositions of the invention encompass liquid compositions and dried forms thereof. For purposes of the present invention, the term "liquid" with regard to pharmaceutical compositions or formulations is intended to include the term "aqueous", and includes liquid formulations that are frozen. By "dried form" is intended the liquid pharmaceutical composition or formulation is dried either by freeze drying (i.e., lyophilization; see, for example, Williams and Polli (1984) *J. Parenteral Sci. Technol.* 38:48-59), spray drying (see Masters (1991) in *Spray-Drying Handbook* (5th ed; Longman Scientific and Technical, Essez, U.K.), pp. 491-676; Broadhead et al. (1992) *Drug Devel. Ind. Pharm.* 18:1169-1206; and Mumenthaler et al. (1994) *Pharm. Res.* 11:12-20), or air drying (Carpenter and Crowe (1988) *Cryobiology* 25:459-470; and Roser (1991) *Biopharm.* 4:47-53). The term "lyophilize" with regard to IFN-β pharmaceutical formulations is intended to refer to rapid freeze drying under reduced pressure of a plurality of vials, each containing a unit dose of the interferon formulation of the present invention therein. Lyophilizers, which perform the above described lyophilization, are commercially available and readily operable by those skilled in the art. In one embodiment of the present invention, the liquid composition is prepared as a lyophilized composition.

In other embodiments of the invention, the HSA-free IFN-β pharmaceutical compositions of the invention can be prepared in a form that is suitable for pulmonary delivery and administering the preparation to the subject via pulmonary inhalation. By "pulmonary inhalation" is intended the pharmaceutical composition is directly administered to the lung by delivering the composition in an aerosol or other suitable preparation from a delivery device into the oral cavity of the subject as the subject inhales through the oral cavity. By "aerosol" is intended a suspension of solid or liquid particles in flowing air or other physiologically acceptable gas stream. Other suitable preparations include, but are not limited to, mist, vapor, or spray preparations so long as the particles comprising the protein composition are delivered in a size range consistent with that described for a dry powder form of the pharmaceutical composition as defined below. Pulmonary inhalation could also be accomplished by other suitable methods known to those skilled in the art. These may include liquid instillation using a suitable device or other such methods. Pulmonary inhalation results in deposition of the inhaled protein composition in the alveoli of the subject's lungs. Once deposited, the protein may be absorbed, passively or actively, across the alveoli epithelium and capillary epithelium layers into the bloodstream for subsequent systemic distribution.

Pulmonary administration of a polypeptide or protein such as IFN-β requires dispensing of the biologically active substance from a delivery device into a subject's oral cavity during inhalation. For purposes of the present invention, HSA-free pharmaceutical compositions comprising IFN-β or variants thereof are administered via inhalation of an aerosol or other suitable preparation that is obtained from an aqueous or nonaqueous solution or suspension form, or a solid or dry powder form of the pharmaceutical composition, depending upon the delivery device used. Such delivery devices are well known in the art and include, but are not limited to, nebulizers, metered-dose inhalers, and dry powder inhalers, or any other appropriate delivery mechanisms that allow for dispensing of a pharmaceutical composition as an aqueous or nonaqueous solution or suspension or as a solid or dry powder form. When used in the context of pharmaceutical compositions suitable for pulmonary delivery, these terms have the following intended meaning. By "aqueous" is intended a composition prepared with, containing, or dissolved in water, including mixtures wherein water is the predominating substance in the mixture. A predominating substance is present in a greater quantity than another component of the mixture. By "non-aqueous" is intended a composition prepared with, containing, or dissolved in a substance other than water or mixtures wherein water is not the predominating substance in the mixture. By "solution" is intended a homogeneous preparation of two or more substances, which may be solids, liquids, gases, or intercombinations thereof. By "suspension" is intended a mixture of substances such that one or more insoluble substances are homogeneously dispersed in another predominating substance.

For purposes of the present invention, the terms "solid" and "dry powder" are used interchangeably with reference to the HSA-free pharmaceutical compositions suitable for pulmonary delivery. By "solid" or "dry powder" form of a pharmaceutical composition is intended the composition has been dried to a finely divided powder having a moisture content below about 10% by weight, usually below about 5% by weight, and preferably below about 3% by weight. This dry powder form of the composition consists of particles comprising the IFN-β or variants thereof. Preferred particle sizes are less than about 10.0 μm mean diameter, more preferably less than about 7.0 μm, even more preferably about less than about 6.0 μm, even more preferably in the range of 0.1 to 5.0 μm, most preferably in the range of about 1.0 to about 5.0 μm mean diameter.

Thus, an HSA-free liquid pharmaceutical composition comprising IFN-β or variants thereof which is intended for pulmonary delivery can either be used as a liquid solution or suspension in the delivery device or first be processed into a dry powder form using lyophilization or spray-drying techniques well known in the art. Where a liquid solution or suspension is used in the delivery device, a nebulizer, a metered dose inhaler, or other suitable delivery device delivers, in a single or multiple fractional dose, by pulmonary inhalation a pharmaceutically effective amount of the composition to the subject's lungs as droplets having the same particle size range noted above for the dry powder form. By "pharmaceutically effective amount" is intended an amount that is useful in the treatment, prevention, or diagnosis of a disease or condition responsive to IFN-β. The liquid solution or suspension of the composition may be used with physiologically appropriate stabilizing agents, excipients, viscosity modifiers, bulking agents, surfactants, or combinations thereof, known to those of skill in the art, so long as they don't compromise the distinguishing characteristics of the HSA-free IFN-β compositions of the invention.

Where the liquid pharmaceutical composition is lyophilized prior to use in pulmonary delivery, the lyophilized composition is milled to obtain the finely divided dry powder consisting of particles within the desired size range noted above. Where spray-drying is used to obtain a dry powder form of the liquid pharmaceutical composition, the process is carried out under conditions that result in a substantially amorphous finely divided dry powder consisting of particles within the desired size range noted above. Similarly, if the starting pharmaceutical composition is already in a lyophilized form, the composition can be milled to obtain the dry powder form for subsequent preparation as an aerosol or other preparation suitable for pulmonary inhalation. Where the starting pharmaceutical composition is in its spray-dried form, the composition has preferably been prepared such that it is already in a dry powder form having the appropriate particle size for dispensing as an aqueous or nonaqueous solution or suspension or dry powder form in accordance pulmonary administration. For methods of preparing dry powder forms of pharmaceutical compositions, see, for example, WO 96/32149, WO 97/41833, WO 98/29096, and U.S. Pat. Nos. 5,976,574, 5,985,248, and 6,001,336; herein incorporated by reference.

The resulting dry powder form of the composition is then placed within an appropriate delivery device for subsequent preparation as an aerosol or other suitable preparation that is delivered to the subject via pulmonary inhalation. Where the dry powder form of the pharmaceutical composition is to be prepared and dispensed as an aqueous or nonaqueous solution or suspension, a metered-dose inhaler, or other appropriate delivery device is used. A pharmaceutically effective amount of the dry powder form of the composition is administered in an aerosol or other preparation suitable for pulmonary inhalation. The amount of dry powder form of the composition placed within the delivery device is sufficient to allow for delivery of a pharmaceutically effective amount of the composition to the subject by inhalation. Thus, the amount of dry powder form to be placed in the delivery device will compensate for possible losses to the device during storage and delivery of the dry powder form of the composition. Following placement of the dry powder form within a delivery device, the properly sized particles as noted above are suspended in an aerosol propellant. The pressurized nonaqueous suspension is then released from the delivery device into the air passage of the subject while inhaling. The delivery device delivers, in a single or multiple fractional dose, by pulmonary inhalation a pharmaceutically effective amount of the composition to the subject's lungs. The aerosol propellant may be any conventional material employed for this purpose, such as a chlorofluorocarbon, a hydrochloro-fluorocarbon, a hydrofluorocarbon, or a hydrocarbon, including trichlorofluoromethane, dichlorodifluromethane, dichlorotetrafluoromethane, dichlorodifluoro-methane, dichlorotetrafluoroethanol, and 1,1,1,2-tetra-fluoroethane, or combinations thereof. A surfactant may be added to the pharmaceutical composition to reduce adhesion of the protein-containing dry powder to the walls of the delivery device from which the aerosol is dispensed. Suitable surfactants for this intended use include, but are not limited to, sorbitan trioleate, soya lecithin, and oleic acid. Devices suitable for pulmonary delivery of a dry powder form of a protein composition as a nonaqueous suspension are commercially available. Examples of such devices include the Ventolin metered-dose inhaler (Glaxo Inc., Research Triangle Park, N.C.) and the Intal Inhaler (Fisons, Corp., Bedford, Mass.). See also the aerosol delivery devices described in U.S. Pat. Nos. 5,522,378, 5,775,320, 5,934,272 and 5,960,792, herein incorporated by reference.

Where the solid or dry powder form of the HSA-free IFN-β pharmaceutical composition is to be delivered as a dry powder form, a dry powder inhaler or other appropriate delivery device is preferably used. The dry powder form of the pharmaceutical composition is preferably prepared as a dry powder aerosol by dispersion in a flowing air or other physiologically acceptable gas stream in a conventional manner. Examples of commercially available dry powder inhalers suitable for use in accordance with the methods herein include the Spinhaler powder inhaler (Fisons Corp., Bedford, Mass.) and the Ventolin Rotahaler (Glaxo, Inc., Research Triangle Park, N.C.). See also the dry powder delivery devices described in WO 93/00951, WO 96/09085, WO 96/32152, and U.S. Pat. Nos. 5,458,135, 5,785,049, and 5,993,783, herein incorporated by reference.

The dry powder form of the HSA-free pharmaceutical composition comprising IFN-β or biologically active variant thereof can be reconstituted to an aqueous solution for subsequent delivery as an aqueous solution aerosol using a nebulizer, a metered dose inhaler, or other suitable delivery device. In the case of a nebulizer, the aqueous solution held within a fluid reservoir is converted into an aqueous spray, only a small portion of which leaves the nebulizer for delivery to the subject at any given time. The remaining spray drains back into a fluid reservoir within the nebulizer, where it is aerosolized again into an aqueous spray. This process is repeated until the fluid reservoir is completely dispensed or until administration of the aerosolized spray is terminated. Such nebulizers are commercially available and include, for example, the Ultravent nebulizer (Mallinckrodt Inc., St. Louis, Mo.) and the Acorn II nebulizer (Marquest Medical Products, Englewood, Colo.). See also the nebulizer described in WO 93/00951, and the device for delivering aerosolized aqueous formulations described in U.S. Pat. No. 5,544,646; herein incorporated by reference.

The HSA-free IFN-β pharmaceutical compositions of the present invention-are "stabilized" compositions. By "stabilized" is intended the compositions retain the IFN-β polypeptide in its substantially monomeric state during storage, and hence the therapeutic effectiveness of this polypeptide is not compromised due to aggregate formation. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. This stability is achieved in the absence of the use of HSA as a stabilizing and solubilizing agent. Preferably, compositions of the invention are stored directly in their liquid form to take full advantage of the convenience of having storage stability in the liquid form, ease of administration without reconstitution, and ability to supply the formulation in prefilled, ready-to-use syringes or as multidose preparations if the formulation is compatible with bacteriostatic agents. The stabilized HSA-free IFN-β compositions of the invention preferably have a shelf-life of at least about 6 months, 12 months, 18 months, more preferably at least 20 months, still more preferably at least about 22 months, most preferably at least about 24 months when stored at 2-8° C.

Methods for monitoring stability of the HSA-free IFN-β pharmaceutical compositions of the invention are available in the art, including those methods described in the examples disclosed herein. Thus, IFN-β aggregate formation during storage of a liquid pharmaceutical composition of the invention can be readily determined by measuring the change in soluble IFN-β in solution over time. Amount of soluble polypeptide in solution can be quantified by a number of analytical assays adapted to detection of IFN-β. Such assays include, for example, reverse phase (RP)-HPLC and UV absorption spectroscopy, as described in the Examples below. Determination of both soluble and insoluble aggregates during storage in liquid formulations can be achieved, for example, using analytical ultracentrifugation as noted in the Examples below to distinguish between that portion of the soluble polypeptide that is present as soluble aggregates and that portion that is present in the nonaggregate, biologically active molecular form.

The stabilized pharmaceutical formulations of the invention comprise IFN-β and variants thereof. The term "IFN-β" as used herein refers to IFN-β or variants thereof, sometimes referred to as IFN-β-like polypeptides. Human IFN-β variants, which may be naturally occurring (e.g., allelic variants that occur at the IFN-β locus) or recombinantly produced, have amino acid sequences that are the same as, similar to, or substantially similar to the mature native IFN-β sequence shown in SEQ ID NO:1. Fragments of IFN-β or truncated forms of IFN-β that retain their activity are also encompassed. These biologically active fragments or truncated forms of IFN-β are generated by removing amino acid residues from the full-length IFN-β amino acid sequence using recombinant DNA techniques well known in the art. IFN-β polypeptides may be glycosylated or unglycosylated, as it has been reported in the literature that both the glycosylated and unglycosylated IFN-β's show qualitatively similar specific activities and that, therefore, the glycosyl moieties are not involved in and do not contribute to the biological activity of IFN-β.

The IFN-β variants encompassed herein include muteins of the mature native IFN-β sequence shown in SEQ ID NO:1, wherein one or more cysteine residues that are not essential to biological activity have been deliberately deleted or replaced with other amino acids to eliminate sites for either intermolecular crosslinking or incorrect intramolecular disulfide bond formation. IFN-β variants of this type include those containing a glycine, valine, alanine, leucine, isoleucine, tyrosine, phenylalanine, histidine, tryptophan, serine, threonine, or methionine substituted for the cysteine found at amino acid 17 of the mature native amino acid sequence. Serine and threonine are the more preferred replacements because of their chemical analogy to cysteine. Serine substitutions are most preferred. In one embodiment shown in SEQ ID NO:2, the cysteine found at amino acid 17 of the mature native sequence shown in SEQ ID NO:1 is replaced with serine. Cysteine 17 may also be deleted using methods known in the art (see, for example, U.S. Pat. No. 4,588,584, herein incorporated by reference), resulting in a mature IFN-β mutein that is one amino acid shorter than the mature native IFN-β. See also, as examples, U.S. Pat. Nos. 4,530,787; 4,572,798; and 4,588,585. Thus, IFN-β variants with one or more mutations that improve, for example, their pharmaceutical utility are also encompassed by the present invention.

The skilled artisan will appreciate that additional changes can be introduced by mutation into the nucleotide sequences encoding IFN-β, thereby leading to changes in the IFN-β amino acid sequence, without altering the biological activity of the interferon. Thus, an isolated nucleic acid molecule encoding an IFN-β variant having a sequence that differs from the amino acid sequence for the mature native IFN-β can be created by introducing one or more nucleotide substitutions, additions, or deletions into the corresponding nucleotide sequence disclosed herein, such that one or more amino acid substitutions, additions or deletions are introduced into the encoded IFN-β. Mutations can be introduced by standard techniques, such as site-directed mutagenesis and PCR-mediated mutagenesis. Such IFN-β variants are also encompassed by the present invention.

For example, conservative amino acid substitutions may be made at one or more predicted, preferably nonessential amino acid residues. A "nonessential" amino acid residue is a residue that can be altered from the wild-type sequence of IFN-β without altering its biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Such substitutions would not be made for conserved amino acid residues, or for amino acid residues residing within a conserved motif.

Alternatively, variant IFN-β nucleotide sequences can be made by introducing mutations randomly along all or part of an IFN-β coding sequence, such as by saturation mutagenesis, and the resultant mutants can be screened for IFN-β biological activity to identify mutants that retain activity. Following mutagenesis, the encoded protein can be expressed recombinantly, and the activity of the protein can be determined using standard assay techniques described herein.

Biologically active variants of IFN-β will generally have at least 80%, more preferably about 90% to about 95% or more, and most preferably about 96% to about 99% or more amino acid sequence identity to the amino acid sequence of mature native IFN-β, which serves as the basis for comparison. By "sequence identity" is intended the same amino acid residues are found within the variant polypeptide and the polypeptide molecule that serves as a reference when a specified, contiguous segment of the amino acid sequence of the variant is aligned and compared to the amino acid sequence of the reference molecule.

For purposes of optimal alignment of the two sequences for the purposes of sequence identity determination, the contiguous segment of the amino acid sequence of the variant may have additional amino acid residues or deleted amino acid residues with respect to the amino acid sequence of the reference molecule. The contiguous segment used for comparison to the reference amino acid sequence will comprise at least 20 contiguous amino acid residues. Corrections for increased sequence identity associated with inclusion of gaps in the variant's amino acid sequence can be made by assigning gap penalties. Methods of sequence alignment are well known in the art.

Thus, the determination of percent identity between any two sequences can be accomplished using a mathematical algorithm. One preferred, non-limiting example of a mathematical algorithm utilized for the comparison of sequences is the algorithm of Myers and Miller (1988) *Comput. Appl. Biosci.* 4:11-7. Such an algorithm is utilized in the ALIGN program (version 2.0), which is part of the GCG alignment software package. A PAM120 weight residue table, a gap length penalty of 12, and a gap penalty of 4 can be used with the ALIGN program when comparing amino acid sequences. Another preferred, non-limiting example of a mathematical algorithm for use in comparing two sequences is the algorithm of Karlin and Altschul (1990) *Proc. Natl. Acad. Sci. USA* 90:5873-5877, modified as in Karlin and Altschul (1993) *Proc. Natl. Acad. Sci USA* 90:5873-5877. Such an algorithm is incorporated into the NBLAST and)(BLAST programs of Altschul et al. (1990) *J. Mol. Biol.* 215:403-410. BLAST amino acid sequence searches can be performed with the XBLAST program, score=50, wordlength=3, to obtain amino acid sequence similar to the polypeptide of interest. To obtain gapped alignments for comparison purposes, gapped BLAST can be utilized as described in Altschul et al. (1997) *Nucleic Acids Res.* 25:3389-3402. Alternatively, PSI-BLAST can be used to perform an integrated search that detects distant relationships between molecules. See Altschul et al. (1997) supra. When utilizing BLAST, gapped BLAST, or PSI-BLAST programs, the default parameters can be used. See www.ncbi.nlm.nih.gov. Also see the ALIGN program (Dayhoff (1978) in *Atlas of Protein Sequence and Structure* 5:Suppl. 3, National Biomedical Research Foundation, Washington, D.C.) and programs in the Wisconsin Sequence Analysis Package, Version 8 (available from Genetics Computer Group, Madison, Wis.), for example, the GAP program, where default parameters of the programs are utilized.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Myers and Miller (1988) *Comput. Appl. Biosci.* 4:11-17.

Biologically active IFN-β variants encompassed by the invention also include IFN-β polypeptides that have been covalently linked with, for example, polyethylene glycol (PEG) or albumin. These covalent hybrid IFN-β molecules possess certain desirable pharmaceutical properties such as an extended serum half-life after administration to a patient. Methods for creating PEG-IFN adducts involve chemical modification of monomethoxypolethylene glycol to create an activated compound that will react with IFN-β. Methods for making and using PEG-linked polypeptides are described, for example in Delgado et al. (1992) *Crit. Rev. Ther. Drug. Carrier Syst.* 9:249-304. Methods for creating albumin fusion polypeptides involve fusion of the coding sequences for the polypeptide of interest (e.g., IFN-β) and albumin and are described in U.S. Pat. No. 5,876,969, herein incorporated by reference.

Biologically active variants of IFN-β encompassed by the invention should retain IFN-β activities, particularly the ability to bind to IFN-β receptors. In some embodiments, the IFN-β variant retains at least about 25%, about 50%, about 75%, about 85%, about 90%, about 95%, about 98%, about 99% or more of the biological activity of the polypeptides whose amino acid sequences are given in SEQ ID NO:1 or 2. IFN-β variants whose activity is increased in comparison with the activity of the polypeptides shown in SEQ ID NO:1 or 2 are also encompassed. The biological activity of IFN-β variants can be measured by any method known in the art. Examples of such assays can be found in Fellous et al. (1982) *Proc. Natl. Acad. Sci USA* 79:3082-3086; Czerniecki et al. (1984) *J. Virol.* 49(2):490-496; Mark et al. (1984) *Proc. Natl. Acad. Sci. USA* 81:5662-5666; Branca et al. (1981) *Nature* 277:221-223; Williams et al. (1979) *Nature* 282:582-586; Herberman et al. (1979) *Nature* 277:221-223; Anderson et al. (1982) *J. Biol. Chem.* 257(19):11301-11304; and the IFN-β potency assay described herein (see Example 2).

The IFN-β of the formulations of the invention can be from any animal species including, but not limited to, avian, canine, bovine, porcine, equine, and human. Preferably, the IFN-β is from a mammalian species when the formulation is to be used in treatment of a mammalian IFN-β disorder, and more preferably is from a mammal of the same species as the mammal undergoing treatment for such a disorder. Thus, where the mammal undergoing treatment is a human, preferably the subject is administered an HSA-free pharmaceutical composition comprising substantially monomeric human IFN-β or biologically active variant thereof.

Non-limiting examples of IFN-β polypeptides and IFN-β variant polypeptides encompassed by the invention are set forth in Nagata et al. (1980) *Nature* 284:316-320; Goeddel et al. (1980) *Nature* 287:411-416; Yelverton et al. (1981) *Nucleic Acids Res.* 9:731-741; Streuli et al. (1981) *Proc. Natl. Acad. Sci. U.S.A.* 78:2848-2852; EP028033B1, and EP109748B1. See also U.S. Pat. Nos. 4,518,584; 4,569,908; 4,588,585; 4,738,844; 4,753,795; 4,769,233; 4,793,995; 4,914,033; 4,959,314; 5,545,723; and 5,814,485. These disclosures are herein incorporated by reference. These citations also provide guidance regarding residues and regions of the IFN-β polypeptide that can be altered without the loss of biological activity.

In one embodiment of the present invention, the IFN-β within the stabilized pharmaceutical formulations is the mature native IFN-β polypeptide. In another embodiment, the IFN-β in these formulations is the mature IFN-β polypeptide wherein the cysteine found at amino acid 17 of the mature native sequence is replaced with serine as discussed above. However, the present invention encompasses other embodiments where the IFN-β within the stabilized pharmaceutical formulation is any biologically active IFN-β polypeptide or variant as described elsewhere herein.

In some embodiments of the present invention, the IFN-β is recombinantly produced. By "recombinantly produced IFN-β" is intended IFN-β that has comparable biological activity to mature native IFN-β and that has been prepared by recombinant DNA techniques. IFN-β can be produced by culturing a host cell transformed with an expression vector comprising a nucleotide sequence that encodes an IFN-β polypeptide. The host cell is one that can transcribe the nucleotide sequence and produce the desired protein, and can be prokaryotic (for example, *E. coli*) or eukaryotic (for example a yeast, insect, or mammalian cell). Examples of recombinant production of IFN-β are given in Mantei et al. (1982) *Nature* 297:128; Ohno et al. (1982) *Nucleic Acids Res.* 10:967; Smith et al. (1983) *Mol. Cell. Biol.* 3:2156, and U.S. Pat. Nos. 4,462,940, 5,702,699, and 5,814,485; herein incorporated by reference. Human interferon genes have been cloned using recombinant DNA ("rDNA") technology and have been expressed in *E. coli* (Nagola et al. (1980) *Nature* 284:316; Goeddel et al. (1980) *Nature* 287:411; Yelverton et al. (1981) *Nuc. Acid Res.* 9:731; Streuli et al. (1981) *Proc. Natl. Acad. Sci. U.S.A.* 78:2848). Alternatively, IFN-β can be produced by a transgenic animal or plant that has been genetically engineered to express the IFN-β protein of interest in accordance with methods known in the art.

Proteins or polypeptides that exhibit native interferon-beta-like properties may also be produced with rDNA technology by extracting poly-A-rich 12S messenger RNA from virally induced human cells, synthesizing double-stranded cDNA using the mRNA as a template, introducing the cDNA into an appropriate cloning vector, transforming suitable microorganisms with the vector, harvesting the microorganisms, and extracting the interferon-beta therefrom. See, for example, European Patent Application Nos. 28033 (published May 6, 1981); 32134 (published Jul. 15, 1981); and 34307 (published Aug. 26, 1981), which describe various methods for the production of interferon-beta employing rDNA techniques.

Alternatively, IFN-β can be synthesized chemically, by any of several techniques that are known to those skilled in the peptide art. See, for example, Li et al. (1983) *Proc. Natl. Acad. Sci. USA* 80:2216-2220, Steward and Young (1984) *Solid Phase Peptide Synthesis* (Pierce Chemical Company, Rockford, Ill.), and Baraney and Merrifield (1980) *The Peptides: Analysis, Synthesis, Biology*, ed. Gross and Meinhofer, Vol. 2 (Academic Press, New York, 1980), pp. 3-254, discussing solid-phase peptide synthesis techniques; and Bodansky (1984) *Principles of Peptide Synthesis* (Springer-Verlag, Berlin) and Gross and Meinhofer, eds. (1980) *The Peptides: Analysis, Synthesis, Biology*, Vol. 1 (Academic Press, New York), discussing classical solution synthesis. IFN-β can also be chemically prepared by the method of simultaneous multiple peptide synthesis. See, for example, Houghten (1984) *Proc. Natl. Acad. Sci. USA* 82:5131-5135; and U.S. Pat. No. 4,631,211.

The recombinantly produced IFN-β for use in preparing the stabilized HSA-free IFN-β pharmaceutical compositions of the invention can be recovered and purified using any method known to one of skill in the art. Such methods include those disclosed in U.S. Pat. Nos. 4,462,940 and 5,702,699, herein incorporated by reference. These methods recover the interferon in a pure form of IFN-β that tends to form aggregates in the absence of SDS, which is used as a solubilizing agent. Further, these methods expose the protein to high pH conditions that may adversely affect the protein's biological properties, and can result in compositions containing residual amounts of SDS used to solubilize the protein during purification. Thus, while the IFN-β may be obtained using these methods, preferably it is recovered and purified by the improved method disclosed in the copending provisional application entitled "Improved Method of Protein Purification and Recovery," filed Oct. 27, 2000, and assigned U.S. Application Ser. No. 60/243,965, copending provisional application entitled "Improved Method of Protein Purification and Recovery," filed Apr. 9, 2001, and assigned U.S. Application Ser. No. 60/282,607, and the provisional application filed concurrently herewith entitled "Methods of Protein Purification and Recovery," and assigned U.S. Application Ser. No. 60/330,375; the contents of which are herein incorporated by reference in their entirety.

Two improved purification and recovery methods for IFN-β are disclosed in these copending and concurrently filed applications. The first of these purification and recovery methods comprises precipitating substantially purified IFN-β with an alcohol such as an aliphatic alcohol, and dissolving the precipitated IFN-β into guanidine hydrochloride. The resulting solution is then diluted into an appropriate buffer to renature the protein. The second of these purification and recovery methods omits the precipitation step. In this manner, a sample comprising substantially purified IFN-β is mixed with guanidine hydrochloride to form a solution comprising solubilized denatured IFN-β; this solution is then diluted into an appropriate buffer to renature the protein. In both methods, the solution comprising renatured IFN-β is then diafiltered or dialyzed into a buffer used for pharmaceutical purposes. When used to prepare an HSA-free pharmaceutical composition of the present invention, the purified renatured IFN-β protein is diafiltered or dialyzed into a low-ionic-strength formulation of the present invention as described in Example 8 below.

Compositions encompassed by the invention may have as little as about 0.01 mg/ml IFN-β and as much as about 20.0 mg/ml IFN-β (weight/volume). In various embodiments, the IFN-β is present at a concentration of about 0.01 mg/ml to about 20.0 mg/ml, about 0.015 mg/ml to about 12.5 mg/ml, about 0.025 mg/ml to about 10.0 mg/ml, about 0.05 mg/ml to about 8.0 mg/ml, about 0.075 mg/ml to about 6.0 mg/ml, about 0.1 mg/ml to about 4.0 mg/ml, about 0.125 mg/ml to about 2.0 mg/ml, about 0.175 mg/ml to about 1.0 mg/ml, about 0.2 mg/ml to about 0.5 mg/ml, about 0.225 mg/ml to about 0.3 mg/ml, and about 0.25 mg/ml.

In some embodiments, the formulations of the invention comprise a pharmaceutically acceptable carrier. By "pharmaceutically acceptable carrier" is intended a carrier that is conventionally used in the art to facilitate the storage, administration, and/or the healing effect of the therapeutic ingredients. A carrier may also reduce any undesirable side effects of the IFN-β. A suitable carrier should be stable, i.e., incapable of reacting with other ingredients in the formulation. It should not produce significant local or systemic adverse effects in recipients at the dosages and concentrations employed for treatment. Such carriers are generally known in the art. Suitable carriers for this invention are those conventionally used large stable macromolecules such as gelatin, collagen, polysaccharide, monosaccharides, polyvinyl-pyrrolidone, polylactic acid, polyglycolic acid, polymeric amino acids, fixed oils, ethyl oleate, liposomes, glucose, lactose, mannose, dextrose, dextran, cellulose, sorbitol, polyethylene glycol (PEG), and the like. Slow-release carriers, such as hyaluronic acid, may also be suitable. See particularly Prisell et al. (1992) *Int. J. Pharmaceu.* 85:51-56, and U.S. Pat. No. 5,166,331.

The pharmaceutical composition may additionally comprise a solubilizing agent or solubility enhancer that contributes to the protein's solubility beyond the enhanced solubility obtained using the low-ionic-strength formulations disclosed herein. Compounds containing a guanidinium group, most preferably arginine, are suitable solubility enhancers for IFN- β. Examples of such solubility enhancers include the amino acid arginine, as well as amino acid analogues of arginine that retain the ability to enhance solubility of IFN-β. Such analogues include, without limitation, dipeptides and tripeptides that contain arginine. Additional suitable solubilizing agents are discussed in U.S. Pat. Nos. 4,816,440; 4,894,330; 5,004,605; 5,183,746; 5,643,566; and in Wang et al. (1980) *J. Parenteral Drug Assoc.* 34:452-462; herein incorporated by reference.

In addition to those agents disclosed above, other stabilizing agents, such as ethylenediaminetetracetic acid (EDTA) or one of its salts such as disodium EDTA, can be added to further enhance the stability of the liquid pharmaceutical compositions. The EDTA acts as a scavenger of metal ions known to catalyze many oxidation reactions, thus providing an additional stabilizing agent. Other suitable stabilizing agents include non-ionic surfactants, including polyoxyethylene sorbitol esters such as polysorbate 80 (Tween 80) and polysorbate 20 (Tween 20); polyoxypropylene-polyoxyethylene esters such as Pluronic F68 and Pluronic F127; polyoxyethylene alcohols such as Brij 35; simethicone; polyethylene glycol such as PEG400; lysophosphatidylcholine; and polyoxyethylene-p-t-octylphenol such as Triton X-100. Classic stabilization of pharmaceuticals by surfactants is described, for example, in Levine et al. (1991) *J. Parenteral Sci. Technol.* 45(3):160-165, herein incorporated by reference.

A pharmaceutically effective amount of a stabilized liquid HSA-free IFN-β formulation or the invention, or of a reconstituted stabilized lyophilized HSA-free IFN-β pharmaceutical formulation of the invention is administered to a subject. By "pharmaceutically effective amount" is intended an amount that is useful in the treatment, prevention, or diagnosis of a disease or condition. Typical routes of administration include, but are not limited to, oral administration, nasal delivery, pulmonary delivery, and parenteral administration, including transdermal, intravenous, intramuscular, subcutaneous, intraarterial, and intraperitoneal injection or infusion. In one such embodiment, the administration is by injection, preferably subcutaneous injection. Injectable forms of the compositions of the invention include, but are not limited to, solutions, suspensions, and emulsions. Typically, a therapeutically effective amount of IFN-β comprises about 0.01 µg/kg to about 5 mg/kg of the composition, preferably about 0.05 µg/kg to about 1000 µg/kg, more preferably about 0.1 µg/kg to about 500 µg/kg, even more preferably still about 0.5 µg/kg to about 30 µg/kg.

In one embodiment, the stabilized HSA-free pharmaceutical composition comprising substantially monomeric IFN-β is formulated in a unit dosage and may be in an injectable or infusible form such as solution, suspension, or emulsion. Furthermore, it can be stored frozen or prepared in the dried form, such as lyophilized powder, which can be reconstituted into the liquid solution, suspension, or emulsion before administration by any of various methods including oral or parenteral routes of administration. The stabilized pharmaceutical composition may be sterilized by membrane filtration and is stored in unit-dose or multi-dose containers such as sealed vials or ampules. Additional methods for formulating a pharmaceutical composition generally known in the art may be used to further enhance storage stability of the pharmaceutical compositions disclosed herein provided they do not adversely affect the beneficial effects of the stabilizing agents as disclosed herein. A thorough discussion of formulation and selection of pharmaceutically acceptable carriers, stabilizers, etc. can be found in *Remington's Pharmaceutical Sciences* (1990) (18th ed., Mack Publishing Company, Eaton, Pa.), herein incorporated by reference.

Formulations comprising an effective amount of the pharmaceutical compositions of the invention comprising β-interferon (IFN-β) or variant thereof, such as the mutein of human IFN-β (hIFN-β) designated hIFN-$β_{ser17}$, are useful in the diagnosis, prevention, and treatment (local or systemic) of clinical indications responsive to therapy with this polypeptide. Such clinical indications include, for example, disorders or diseases of the central nervous system (CNS), brain, and/or spinal cord, including Alzheimer's disease, Parkinson's disease, Lewy body dementia, multiple sclerosis, epilepsy, cerebellar ataxia, progressive supranuclear palsy, amyotrophic lateral sclerosis, affective disorders, anxiety disorders, obsessive compulsive disorders, personality disorders, attention deficit disorder, attention deficit hyperactivity disorder, Tourette Syndrome, Tay Sachs, Nieman Pick, and schizophrenia; nerve damage from cerebrovascular disorders such as stroke in the brain or spinal cord, from CNS infections including meningitis and HIV, from tumors of the brain and spinal cord, or from a prion disease; autoimmune diseases, including acquired immune deficiency, rheumatoid arthritis, psoriasis, Crohn's disease, Sjogren's syndrome, amyotropic lateral sclerosis, and lupus; and cancers, including breast, prostate, bladder, kidney and colon cancers. Administration of IFN-β or its muteins to humans or animals may be delivered orally, intraperitoneally, intramuscularly, subcutaneously, intravenously, intranasally, or by pulmonary delivery as deemed appropriate by the physician.

The present invention provides a method for increasing solubility of interferon-beta (IFN-β) or biologically active variant thereof in a pharmaceutical composition in the absence of human serum albumin. The method comprises preparing the composition with a low-ionic-strength formulation as disclosed elsewhere herein such that the pH of the composition is maintained at about pH 3.0 to about pH 5.0, and incorporating the IFN-β or biologically active variant thereof into the composition. In one embodiment, the low-ionic-strength formulation comprises glycine, aspartic acid, or sodium succinate as the buffer at a concentration of about 1 mM to about 30 mM, preferably about 2 mM to about 5 mM. The composition may further comprise a non-ionic tonicifying agent in an amount sufficient to render the composition isotonic with body fluids as disclosed elsewhere herein. In one embodiment, the non-ionic tonicifying agent is selected from the group consisting of trehalose, sucrose, mannitol, and any combination thereof. Further, by maintaining the pH of this composition between about pH 3.0 and pH 5.0, preferably pH 4.0, it is possible to retain the majority of the IFN-β in its monomeric state. Thus the invention also provides a method for preparing a stabilized HSA-free pharmaceutical composition comprising substantially monomeric IFN-β.

The following examples are offered by way of illustration and not by way of limitation.

EXPERIMENTAL

The current invention was made by better understanding the solubility and stability properties of IFN-β-1b. The preferred characteristics of the HSA free IFN-β-1b formulations are a pH range of about pH 3.0 to about pH 5.0 and very low-ionic-strength conditions. The use of very low-ionic-strength conditions within this pH range results in a higher content of monomeric IFN-β-1b and lower content of aggregated IFN-β-1b species. These conditions provide for IFN-β-1b solubility and stability not previously attainable without the use of HSA in the formulation. They also provide for formulations having the maximum content of monomeric IFN-β-1b.

IFN-β-1b for use in these experiments was produced in *E. coli* essentially as described in the first several steps of purification set forth in U.S. Pat. Nos. 4,462,940 and/or 4,816,400. That is, transformed bacteria were used to produce IFN-β; the host cells were concentrated, and their cell walls disrupted to obtain IFN-β-1b bulk material.

The IFN-β-1b bulk material so obtained contains 50 mM sodium acetate, 1 mM EDTA, 0.1% sodium dodecyl sulfate (SDS) at pH 5.5. To create the starting material for solubility and stability measurements described below, SDS was removed from the IFN-β-1b bulk material by processing the material through a G-25 column (Pharmacia) equilibrated with 1.5 mM sodium hydroxide at >pH 11. After collecting the pool from the G-25 column, a volume of 1 M glycine, pH 3, equal to approximately 1/10 of the pool was added with rapid stirring to adjust the pool to ~pH 3. Materials were stored at 4° C. or frozen for subsequent use in solubility and stability measurements.

Example 1

Determining the Solubility of IFN-β-1b

Initial experiments were conducted to understand the solubility of IFN-β-1b under a wide variety of conditions of pH, buffer type, and ionic strength. A solution of IFN-β-1b (~0.8 mg/ml IFN-β-1b in 100 mM glycine, pH 3.0) was dialyzed against the buffers in Table 1. Results are shown in FIG. 1. These results show that the solubility of IFN-β-1b is dependent upon pH and ionic strength. The IFN-β-1b at pH 3.0 remains soluble at all concentrations of sodium chloride to 200 mM. For formulations at pH 4.0, the IFN-β-1b becomes less soluble as the sodium chloride concentration reaches 150 mM. For formulations at pH 5.0, IFN-β-1b becomes less soluble when the formulation contains only 100 mM sodium chloride. Taken together, these data indicate that IFN-β-1b is most soluble in formulations at pH 3.0, less soluble in formulations at pH 4.0, and least soluble at pH 5.0. These data also indicate that increasing the ionic strength of formulations (by increasing the sodium chloride concentration) also decreases the solubility of IFN-β-1b.

Figure 2:
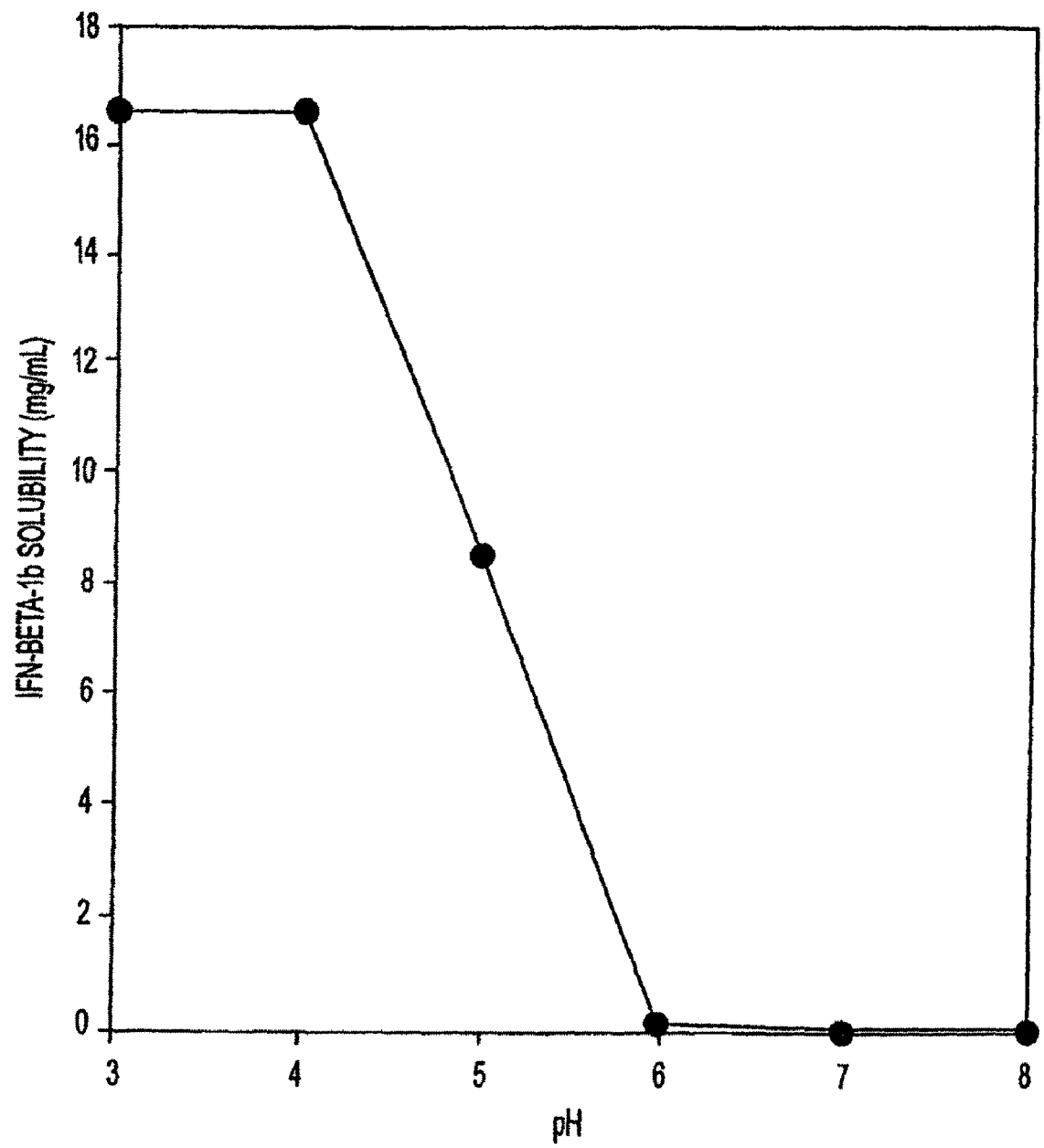
FIG. 2 shows IFN-β-1b solubility in low-ionic-strength formulations.

While the above experiment was able to determine conditions favorable for IFN-β-1b solubility, it did not determine the solubility limit at any of the given conditions. A subsequent experiment was conducted to determine the solubility limits of IFN-β-1b. To maximize IFN-β-1b, low-ionic-strength formulations were used (i.e., 5 mM buffer and no salts such as sodium chloride). After dialysis, IFN-β-1b was concentrated to determine the solubility limit in a given formulation. Results of these experiments are shown in FIG. 2. Formulations at pH 3.0 and 4.0 are most soluble, showing a solubility of at least 16 mg/ml. The formulation at pH 5 was soluble to approximately 8 mg/ml. Formulations above pH 5.0 were soluble only to approximately 0.2 mg/ml. These results again indicate that pH has a powerful effect on IFN-β-1b solubility. Low-ionic-strength formulations at pH 3.0 and pH 4.0 are more soluble than at pH 5.0. Above pH 5.0, IFN-β-1b is essentially insoluble in low-ionic-strength formulations.

TABLE 1

Formulations to Examine IFN-β-1b Solubility pH, Buffer Type and Sodium Chloride Concentration

| Buffer | pH | Sodium Chloride Concentration (mM) |
| --- | --- | --- |
| 5 mM Glycine | pH 3 | 0 mM |
| 5 mM Glycine | pH 3 | 50 mM |
| 5 mM Glycine | pH 3 | 100 mM |
| 5 mM Glycine | pH 3 | 150 mM |
| 5 mM Citrate | pH 4 | 0 mM |
| 5 mM Citrate | pH 4 | 50 mM |
| 5 mM Citrate | pH 4 | 100 mM |
| 5 mM Citrate | pH 4 | 150 mM |
| 5 mM Acetate | pH 4 | 0 mM |
| 5 mM Acetate | pH 4 | 50 mM |
| 5 mM Acetate | pH 4 | 100 mM |
| 5 mM Acetate | pH 4 | 150 mM |
| 5 mM Formate | pH 4 | 0 mM |
| 5 mM Formate | pH 4 | 50 mM |
| 5 mM Formate | pH 4 | 100 mM |
| 5 mM Formate | pH 4 | 150 mM |
| 5 mM Acetate | pH 5 | 0 mM |
| 5 mM Acetate | pH 5 | 50 mM |
| 5 mM Acetate | pH 5 | 100 mM |
| 5 mM Acetate | pH 5 | 150 mM |
| 5 mM Histidine | pH 5 | 0 mM |
| 5 mM Histidine | pH 5 | 50 mM |
| 5 mM Histidine | pH 5 | 100 mM |
| 5 mM Histidine | pH 5 | 150 mM |
| 5 mM Sodium succinate | pH 5 | 0 mM |
| 5 mM Sodium succinate | pH 5 | 50 mM |
| 5 mM Sodium succinate | pH 5 | 100 mM |
| 5 mM Sodium succinate | pH 5 | 150 mM |

Example 2

Analytical Ultracentrifugation Experiments

Figure 6:
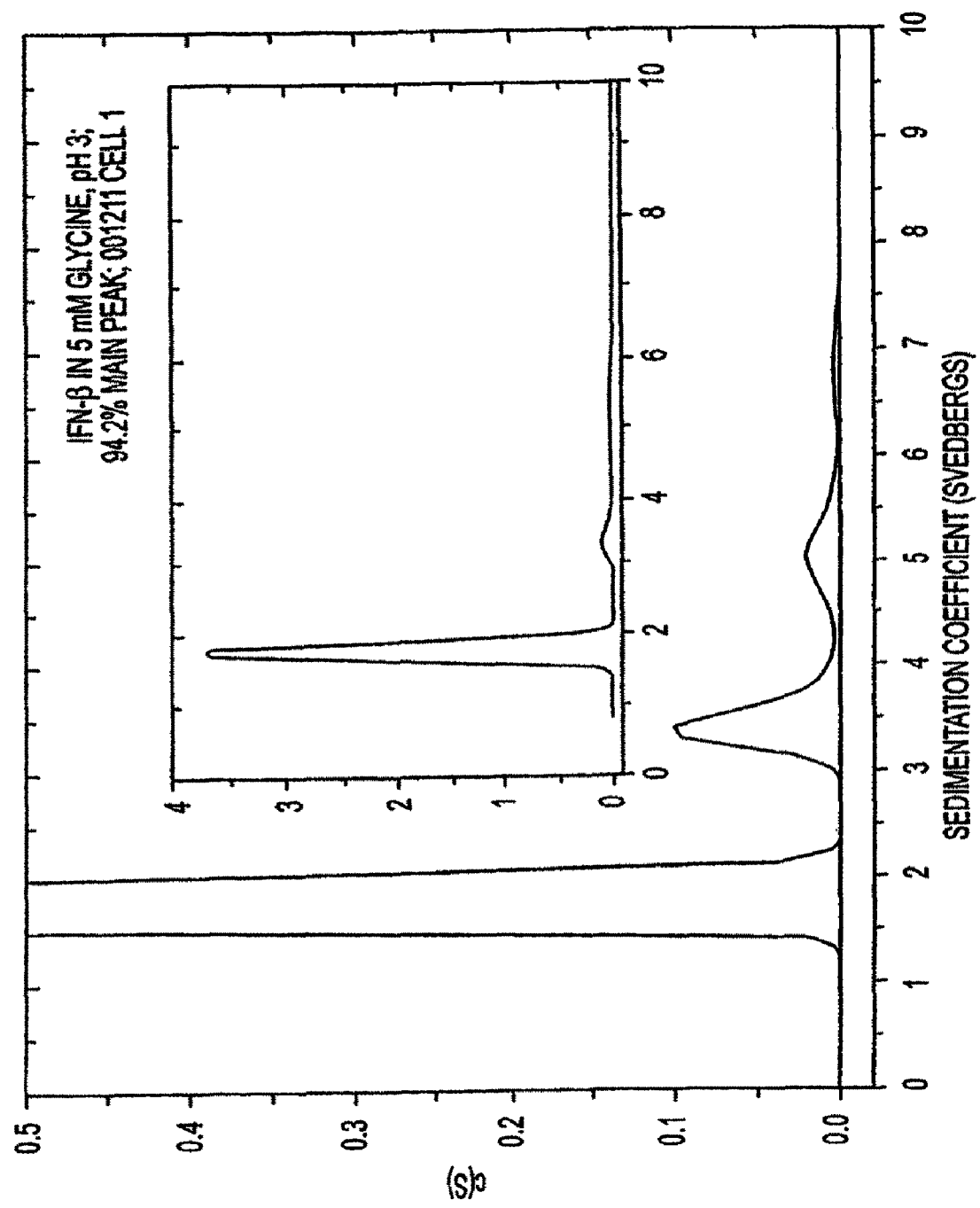
FIG. 6 shows the effect of ionic strength (0 mM NaCl) on the IFN-β-1b aggregation state.
Figure 9:
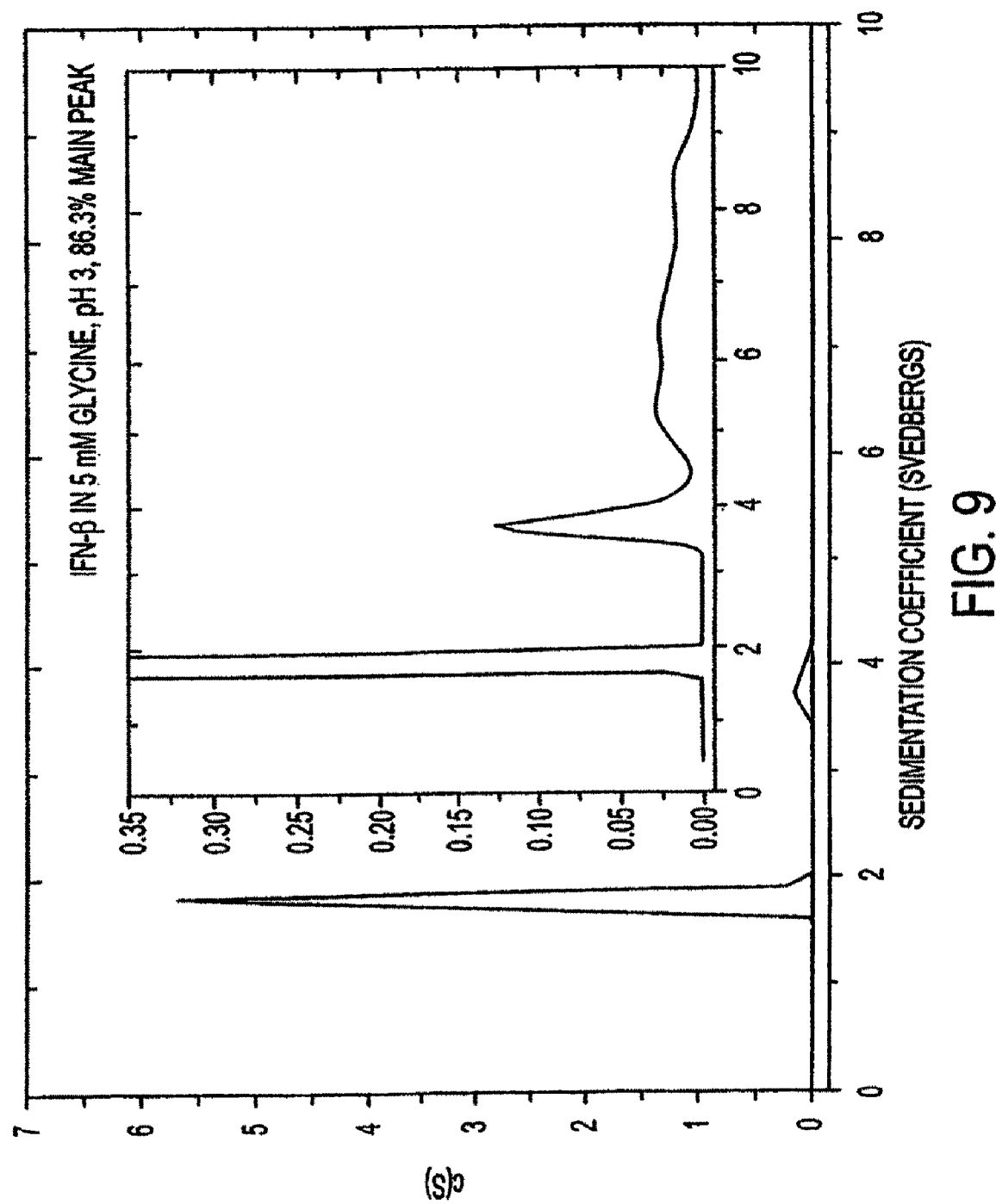
FIG. 9 shows aggregation state of IFN-β-1b in a pH 3.0 formulation containing only the 5 mM glycine buffering agent.

While solubility experiments can determine how much IFN-β-1b is in solution, other techniques are required to determine the aggregation state of the protein. It is important to determine whether a protein is monomeric in a given formulation and to determine how much of the protein (if any) exists in higher ordered forms such as dimers, trimers, etc. Analytical ultracentrifugation is one of the most powerful techniques for elucidating the aggregation state of proteins (see Liu and Shire (1999) *J. Pharm. Sci.* 88:1237-1241). Three experiments were conducted to characterize the monomeric content of several IFN-β-1b formulations with the use of analytical ultracentrifugation. These analytical ultracentrifugation experiments were each conducted with a different preparation of IFN-β-1b. In this matter, each experiment contained a common formulation (5 mM glycine, pH 3.0). However, each of these common formulations varied slightly in the percent monomer (FIG. 3—89.8%; FIG. 6—94.2%; FIG. 9—86.3%). The recovery and purification procedure used to prepare these IFN-β-1b formulations produces some aggregation of the IFN-β-1b molecule, which is mainly covalent in nature. The 5 mM glycine, pH 3.0 formulation for each experiment therefore serves as the baseline for the amount of aggregate in the formulation at the beginning of each experiment.

Figure 3:
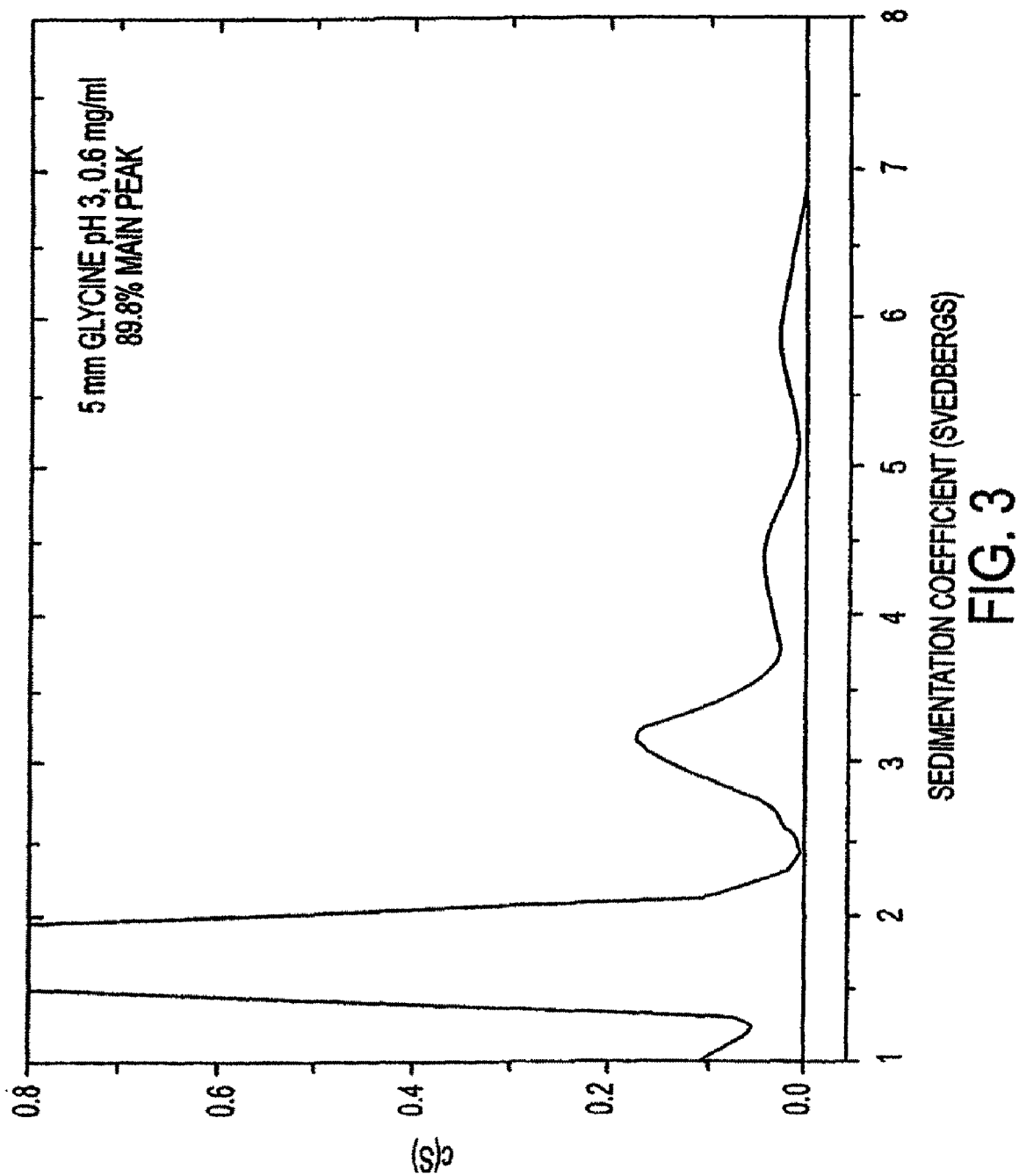
FIG. 3 shows the effect of pH 3.0 on the IFN-β-1b aggregation state.
Figure 4:
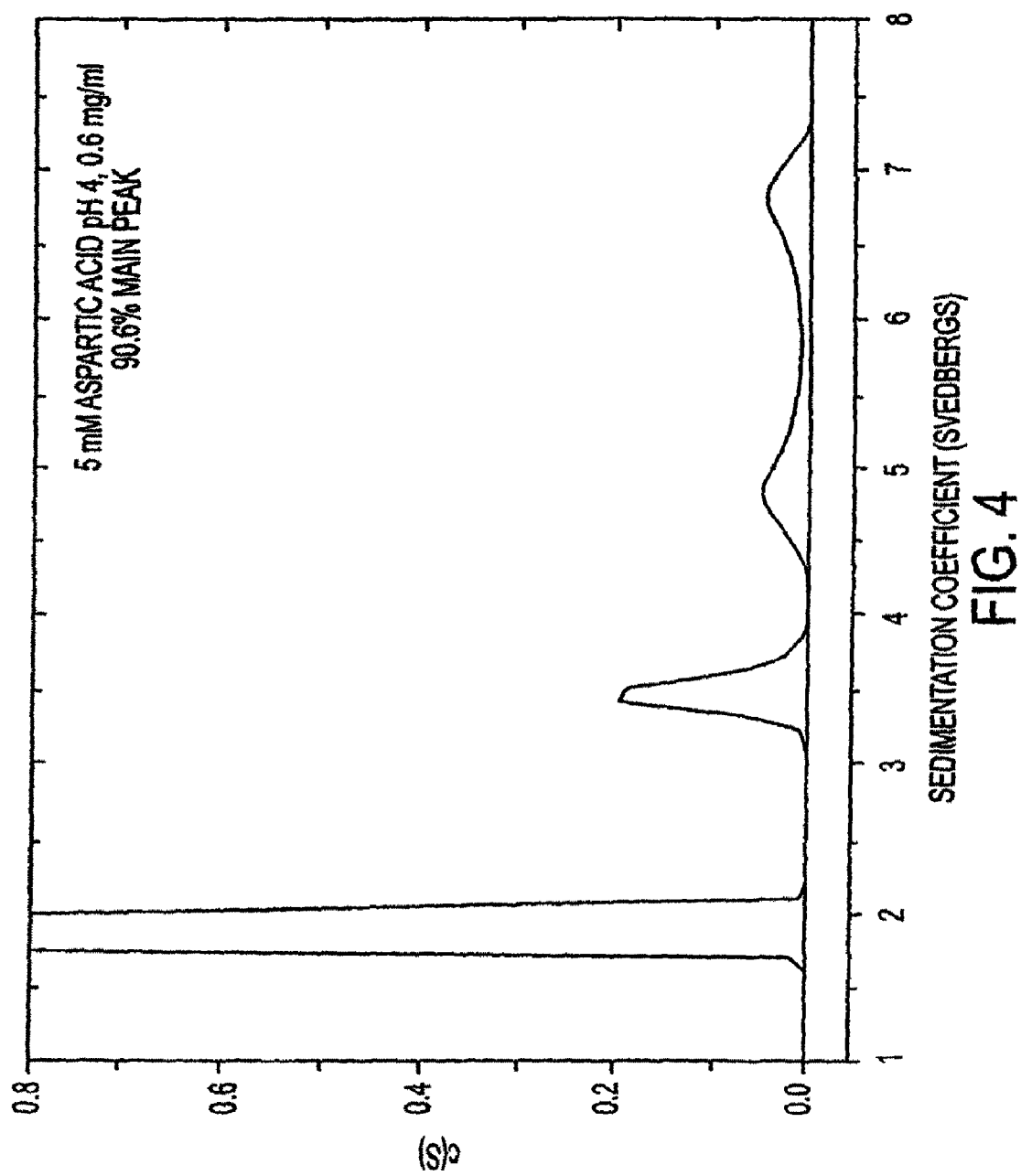
FIG. 4 shows the effect of pH 4.0 on the IFN-β-1b aggregation state.
Figure 5:
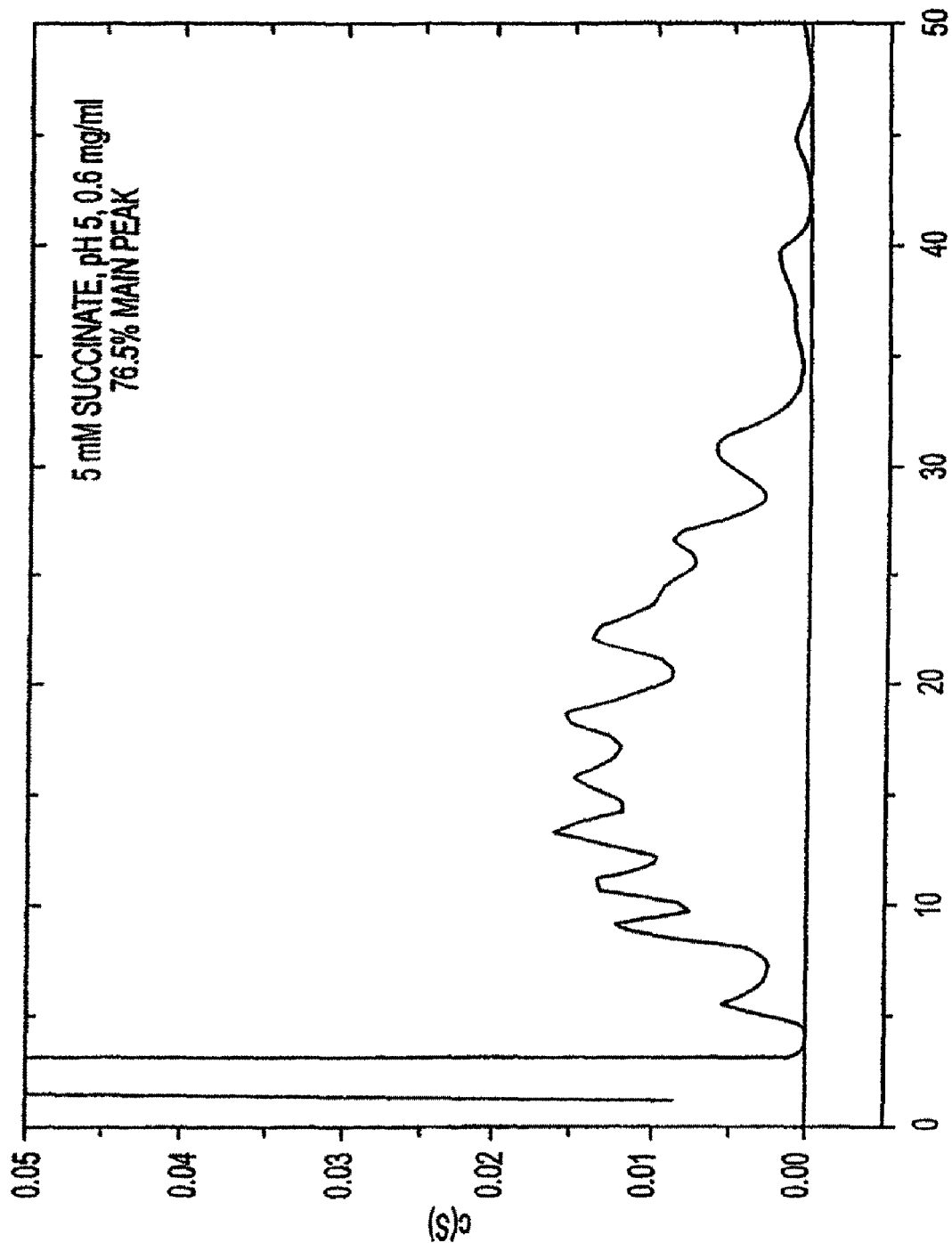
FIG. 5 shows the effect of pH 5.0 on the IFN-β-1b aggregation state.

The first experiment examined the effect of pH on the IFN-β-1b aggregation state. Formulations at pH 3.0 (containing only 5 mM glycine to buffer the solution), pH 4.0 (containing only 5 mM aspartic acid to buffer the solution), and pH 5.0 (containing only 5 mM sodium succinate to buffer the solution were analyzed. Results are shown in FIGS. 3, 4 and 5. The main peak in these profiles corresponds to molecular weight of approximately 20 kDa, which is very close to the molecular weight of IFN-β-1b (19.878 kDa). The main peak is therefore the IFN-β-1b monomer. Larger species (dimers, trimers, etc.) correspond to higher sedimentation coefficients. These results show that while IFN-β-1b is mainly monomeric at pH 3.0 and pH 4.0 (about 90%), at pH 5.0 the molecule begins to aggregate into higher ordered species and is only about 75% monomeric. These results indicate that the aggregation state of IFN-β-1b is susceptible to changes in pH, and that the IFN-β-1b monomer is favored by low pH conditions such as pH 3.0 and pH 4.0.

Figure 7:
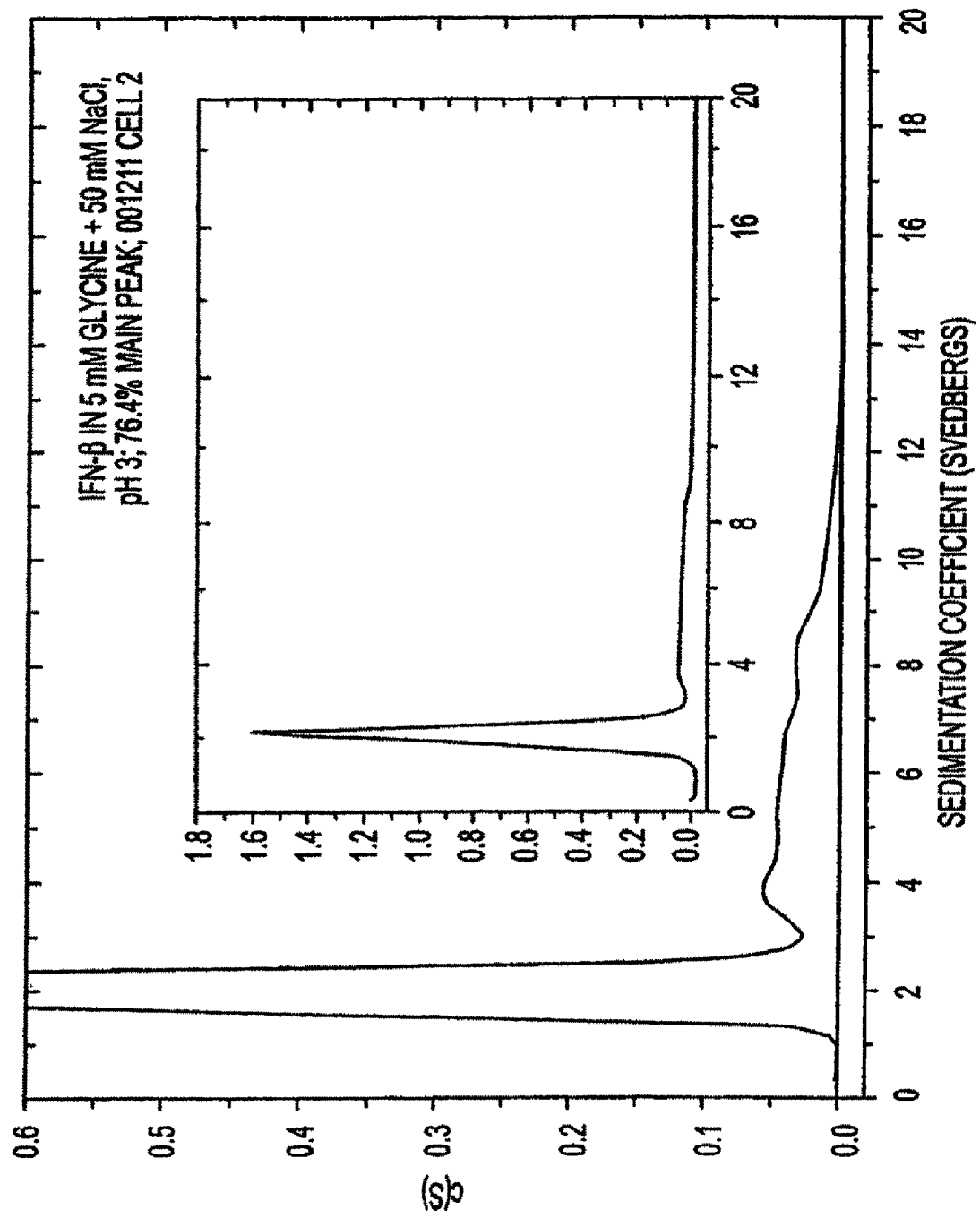
FIG. 7 shows the effect of ionic strength (50 mM NaCl) on the IFN-β-1b aggregation state.
Figure 8:
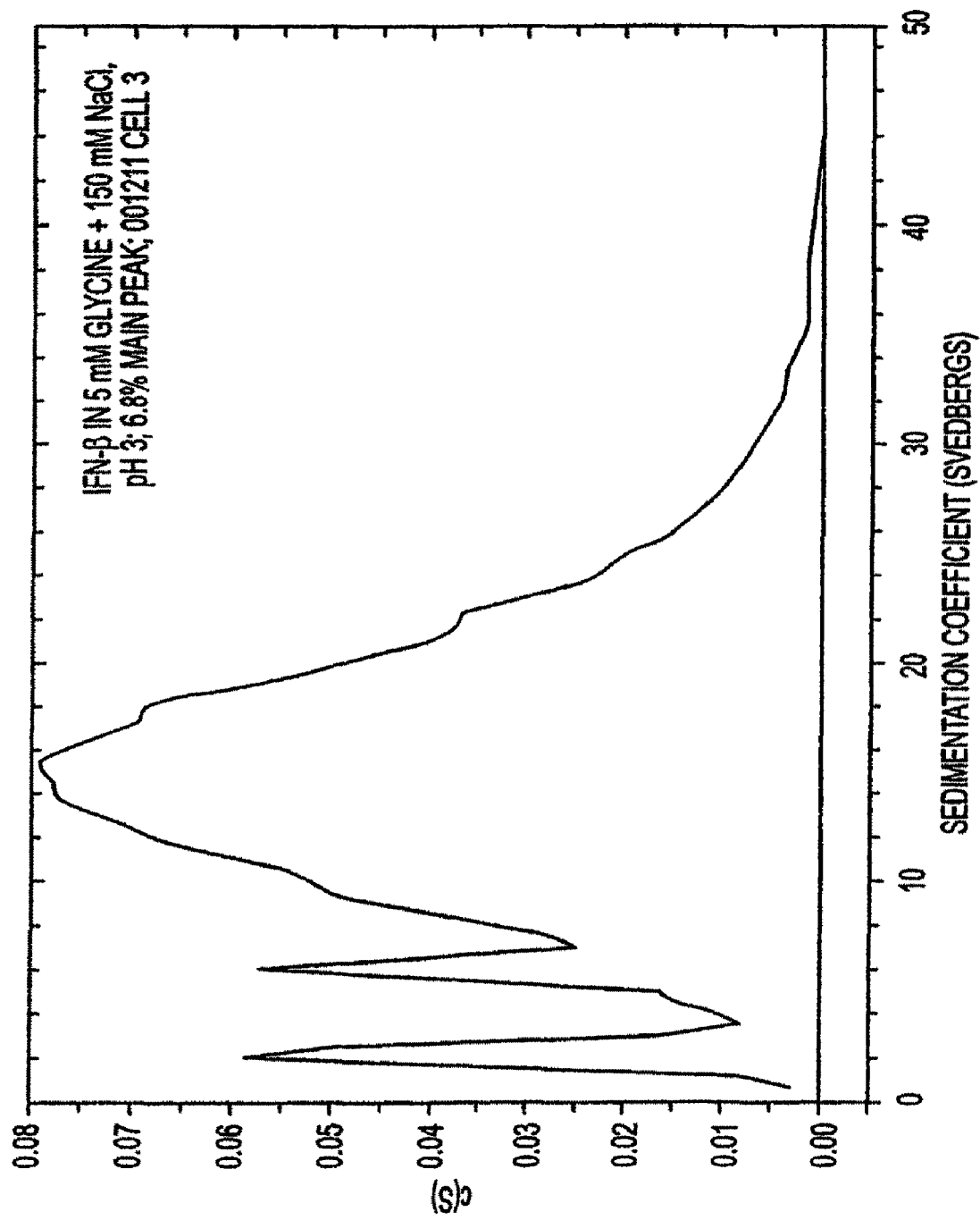
FIG. 8 shows the effect of ionic strength (150 mM NaCl) on the IFN-β-1b aggregation state.

The second experiment investigated the effect of ionic strength on the IFN-β-1b aggregation state. The ionic strength of the formulation was increased in formulations at pH 3.0 (buffered with 5 mM glycine) by adding 0, 50 mM, and 150 mM sodium chloride. Results are shown in FIGS. 6, 7, and 8. For the formulation containing no added sodium chloride (FIG. 6), the monomeric form of IFN-β-1b comprises about 94% of the total IFN-β-1b (i.e., 94% main peak). When 50 mM sodium chloride is added to the formulation, the monomer content drops to about 76% (FIG. 7), and with 150 mM sodium chloride in the formulation, the monomer drops to less than 10% (FIG. 8). These results indicate that the aggregation state of IFN-β-1b is strongly susceptible to ionic strength and that IFN-β-1b monomer is favored by low-ionic-strength conditions.

Figure 10:
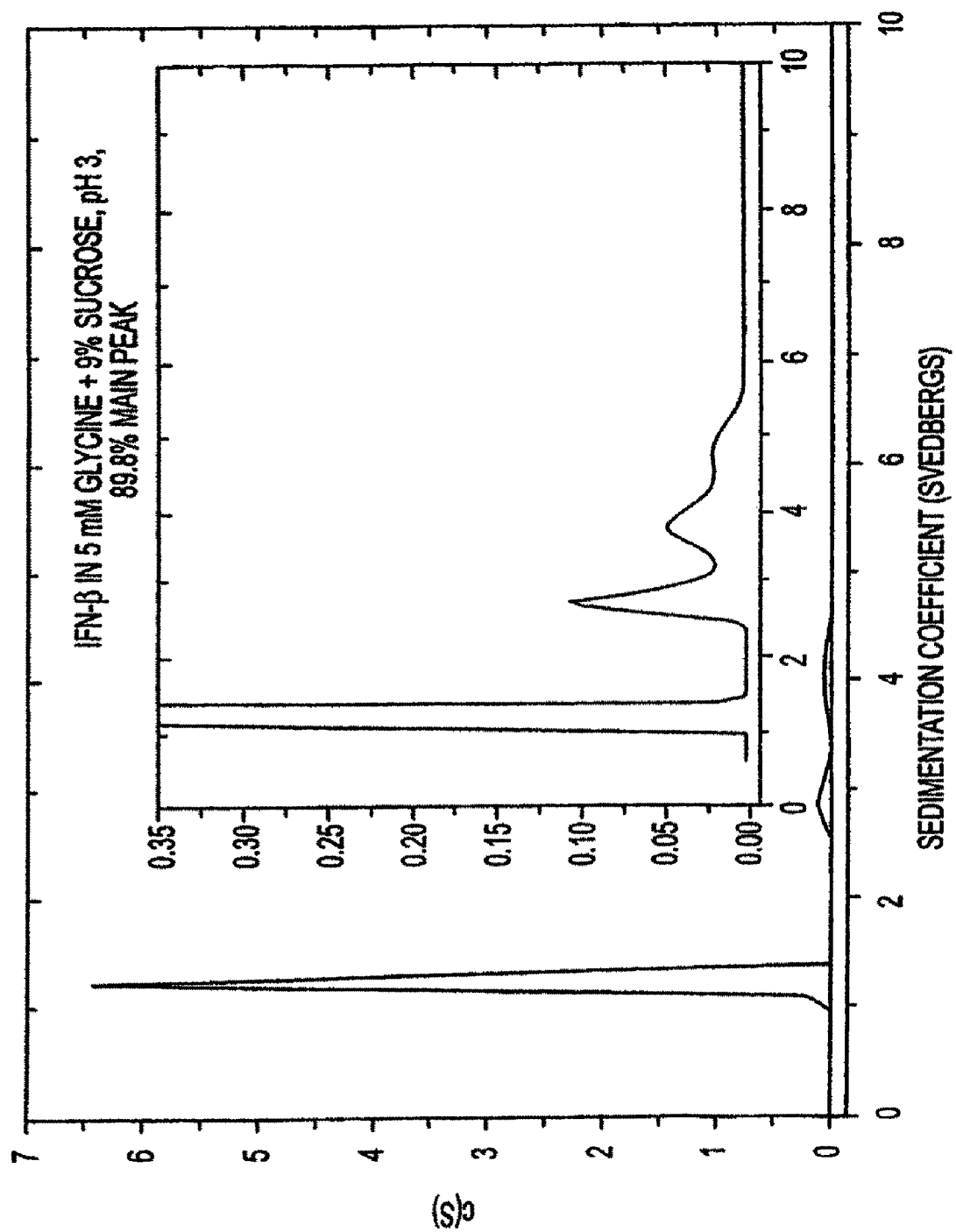
FIG. 10 shows the effect of a non-ionic tonicifying agent (9% sucrose) on the aggregation state of IFN-β-1b in the formulation shown in FIG. 9.
Figure 11:
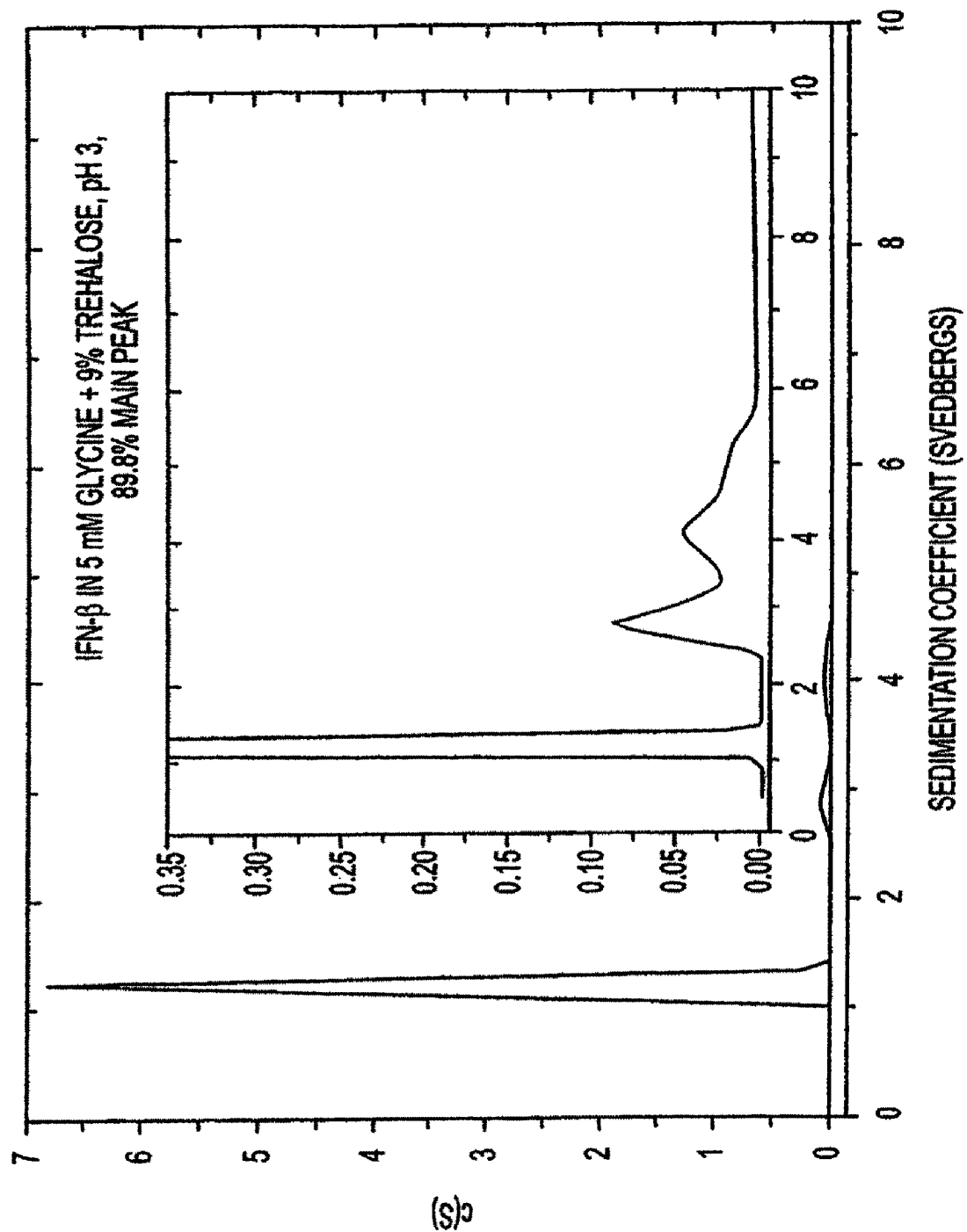
FIG. 11 shows the effect of a non-ionic tonicifying agent (9% trehalose) on the aggregation state of IFN-β-1b in the formulation shown in FIG. 9.

A desirable characteristic of an injectable pharmaceutical formulation is that it should be isotonic with body fluids. Ionic substances (such as sodium chloride) and non-ionic substances (such as the sugars sucrose and trehalose) may be used to make the formulation isotonic with body fluids. The previous analytical ultracentrifugation experiments examined formulations that were either not isotonic (containing only 5 mM buffer) or contained sodium chloride as an ionic tonicifier. A third experiment examined the effect of non-ionic tonicifying agents on the aggregation state of IFN-β-1b. In this experiment three formulations at pH 3.0 (buffered with 5 mM glycine) were prepared. One contained only the glycine buffering agent, the second was tonicified with 9% sucrose, and a third was tonicified with 9% trehalose. Analytical ultracentrifugation results are shown in FIGS. 9, 10, and 11. The monomer content of the formulation with the buffering agent only (FIG. 9) is about 86%. When adding either sucrose (FIG. 10) or trehalose (FIG. 11) as the tonicifying agent, the monomer content is about 89%. These results indicate that non-ionic tonicifying agents such as sucrose and trehalose do not promote aggregation of the IFN-β-1b molecule.

Example 3

Stability of Lyophilized IFN-β-1b HSA Free Formulations Under Accelerated Temperature Conditions HSA-free formulations of IFN-β-1b at pH 3.0 (5 mM glycine as buffer) and pH 4.0 (5 mM aspartic acid as buffer) containing either 9% trehalose (pH 3.0 and pH 4.0) or 9% sucrose (pH 4.0) were lyophilized. The lyophilized formulations were then stored at 40° C. and their stability measured over 8 weeks. Sucrose and trehalose are typical stabilizing agents used in lyophilized formulations. A level of 9% of these reagents is used so that the reconstituted formulation will be isotonic with body fluids. To minimize the ionic strength of the formulations and thus the amount of aggregated IFN-β-1b, the amount of buffer was kept to a minimum level. Thus, all buffers were at a concentration of 5 mM.

Figure 12:
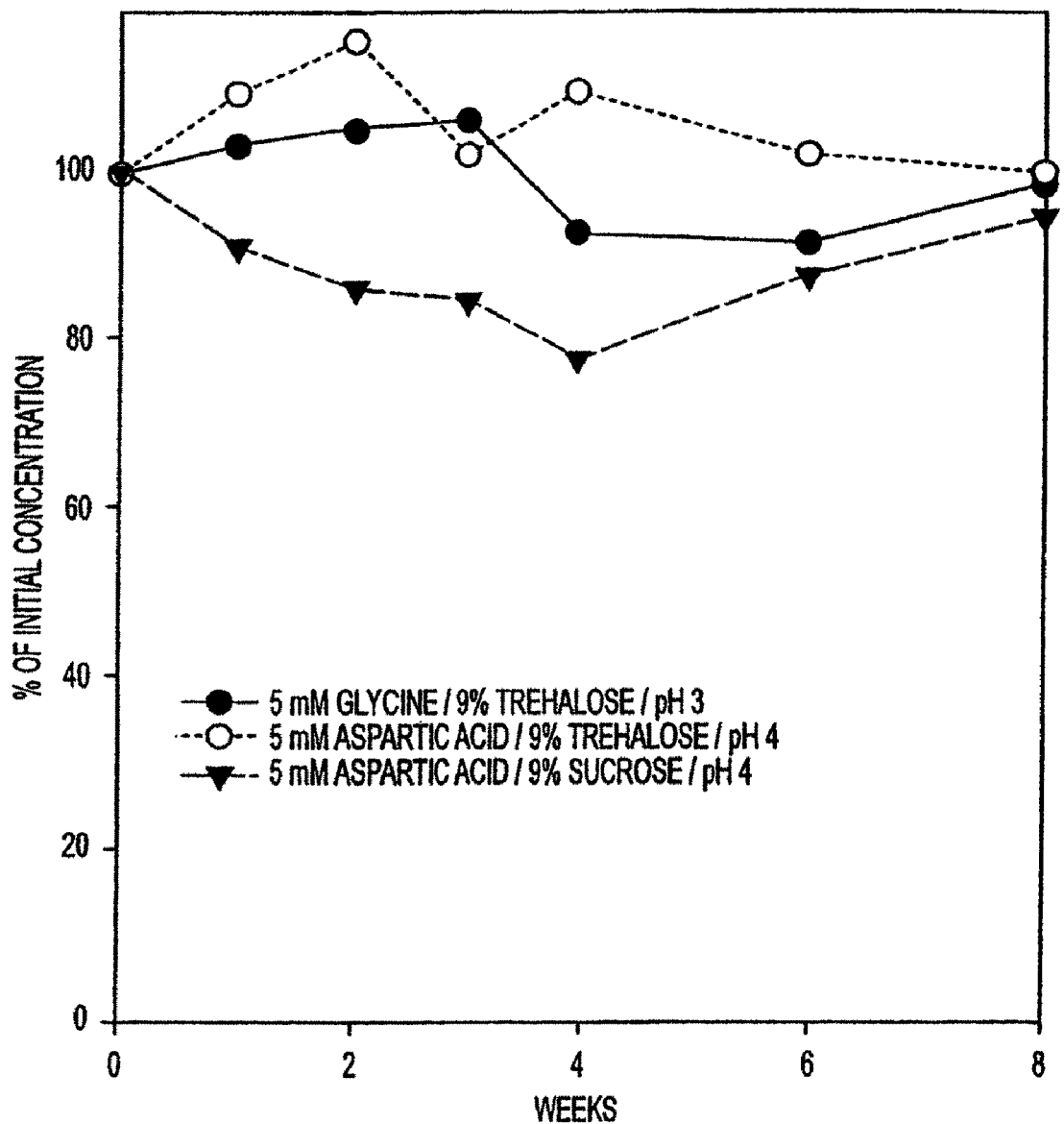
FIG. 12 shows percent of initial IFN-β-1b concentration in lyophilized formulations containing 9% trehalose or 9% sucrose following 8-weeks storage at 40° C. Concentration was determined by UV absorption.
Figure 13:
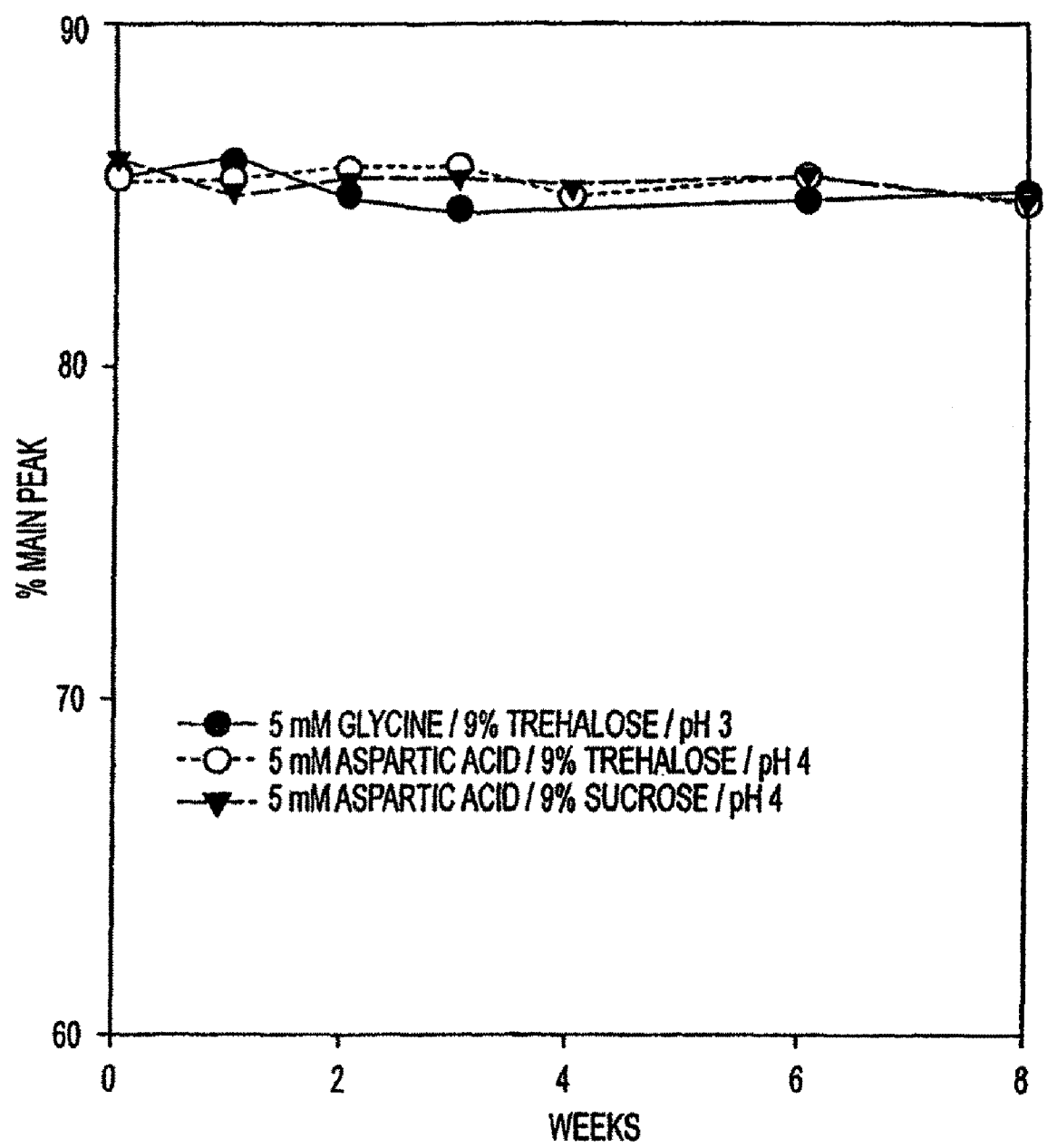
FIG. 13 shows percent of main peak IFN-β-1b in lyophilized formulations containing 9% trehalose or 9% sucrose following 8-weeks storage at 40° C. Percent of main peak was determined by RP-HPLC analysis.

The typical storage condition for protein pharmaceutical products is often 5° C. However, accelerated temperature conditions are often used in formulation studies to increase the rate of degradation of a particular formulation so that relevant stability data can be collected in a shorter period of time. In this experiment, 40° C. was used to attempt the forced degradation of IFN-β-1b in HSA-free formulations. Results for concentration measurements and reverse-phase HPLC (RP-HPLC) analysis are shown in FIGS. 12 and 13. These results show that even at elevated temperatures, these IFN-β-1b formulations show no detectable changes over the 8-week study.

Example 4

Figure 14:
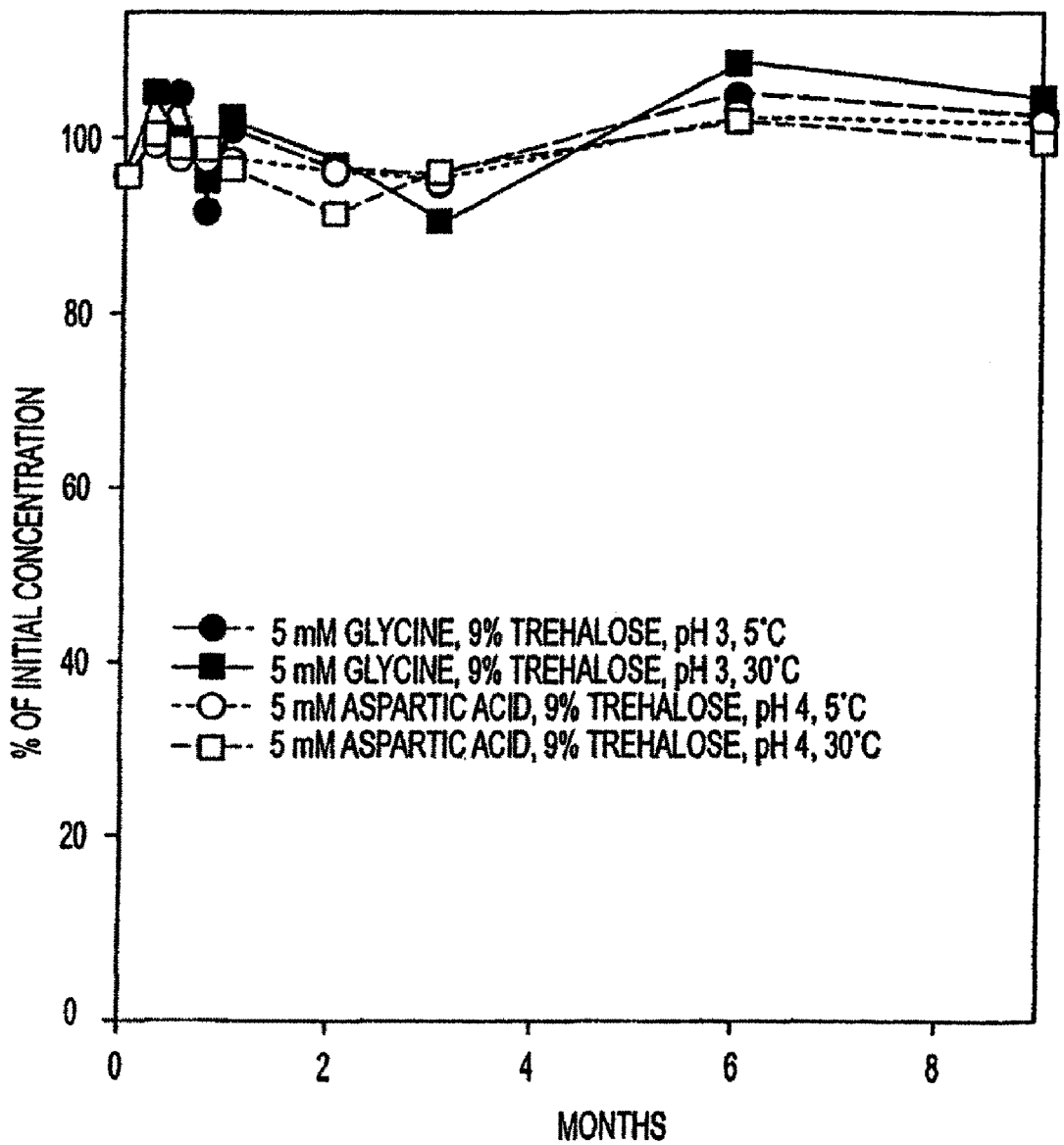
FIG. 14 shows percent of initial IFN-β-1b concentration in lyophilized formulations containing 9% trehalose following 9-months storage at 5° C. or 30° C. Concentration was determined by UV spectroscopy.
Figure 15:
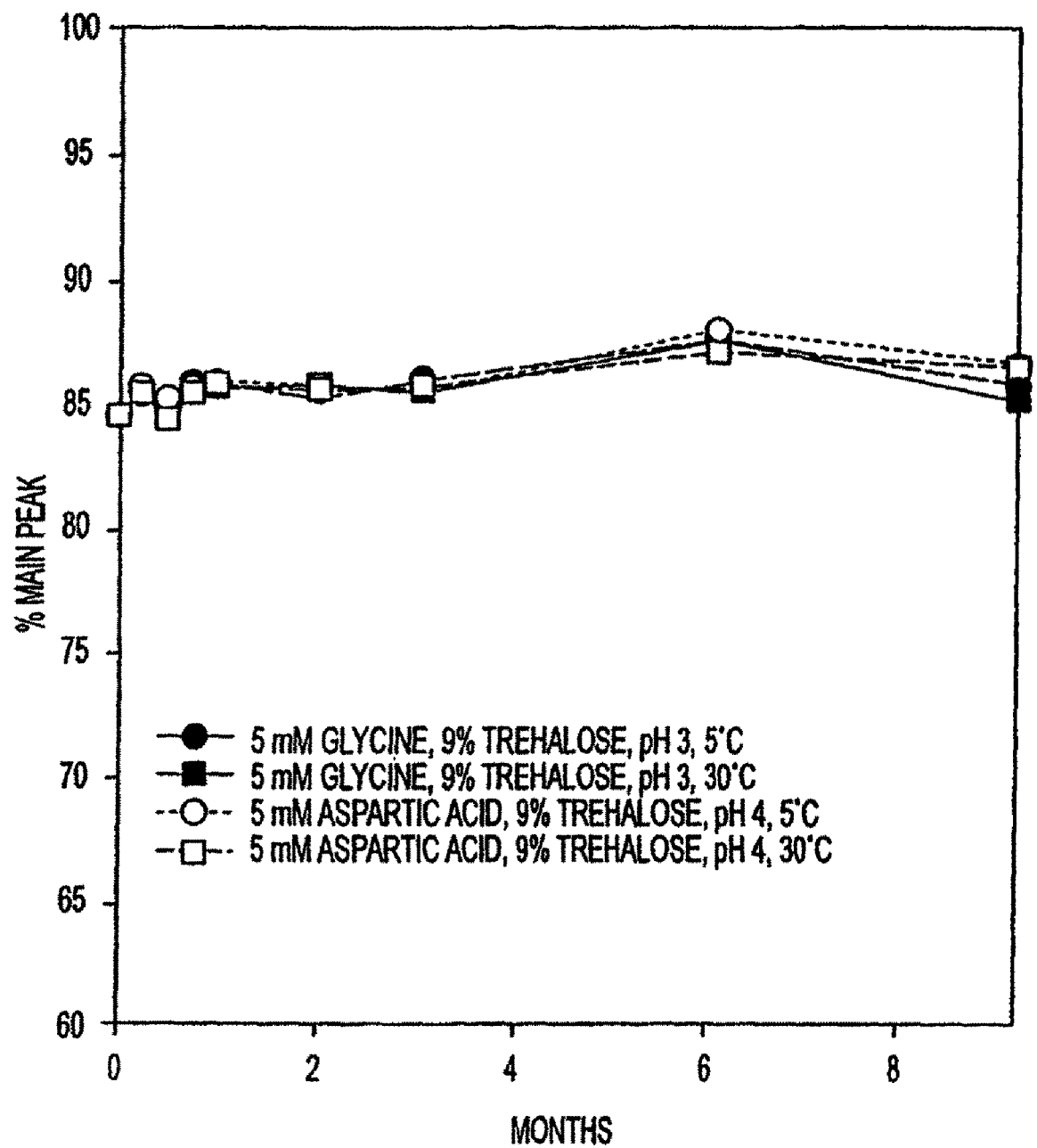
FIG. 15 shows percent of main peak IFN-β-1b in lyophilized formulations containing 9% trehalose following 9-months storage at 5° C. or 30° C. Percent main peak was determined by RP-HPLC analysis.

Stability of Lyophilized IFN-β-1b HSA-Free Formulations Containing Trehalose Under Real Time Storage Conditions Although a typical storage condition for protein pharmaceuticals is 5° C., it is desirable to have a product with room temperature stability (25° C. to 30° C.). In this experiment, formulations containing 9% trehalose (5 mM glycine, pH 3, or 5 mM aspartic acid, pH 4) were lyophilized. A concentration of 9% trehalose was used so that the reconstituted formulation would be isotonic with body fluids. Formulations were stored at 5° C. and 30° C. and their stability measured over 9 months. Results for concentration measurements and reverse-phase HPLC (RP-HPLC) analysis are shown in FIG. 14 and FIG. 15. These results show that even at 30° C., these IFN-β-1b formulations show no detectable changes over the 9 months of the study.

Example 5

Figure 16:
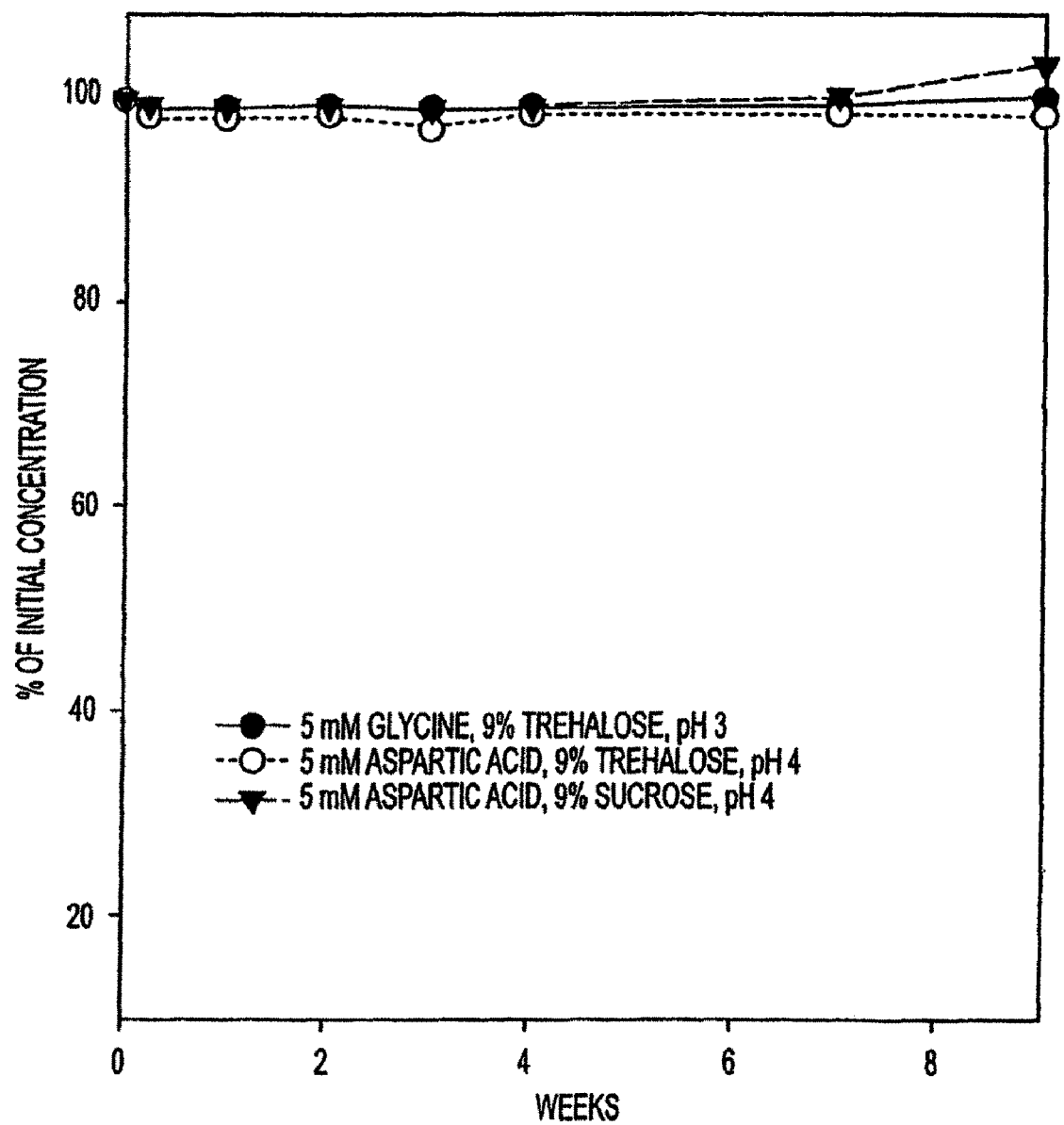
FIG. 16 shows percent of initial IFN-β-1b concentration in liquid formulations containing 9% trehalose or 9% sucrose following 9-weeks storage at 30° C. Concentration was determined by UV absorbance.
Figure 17:
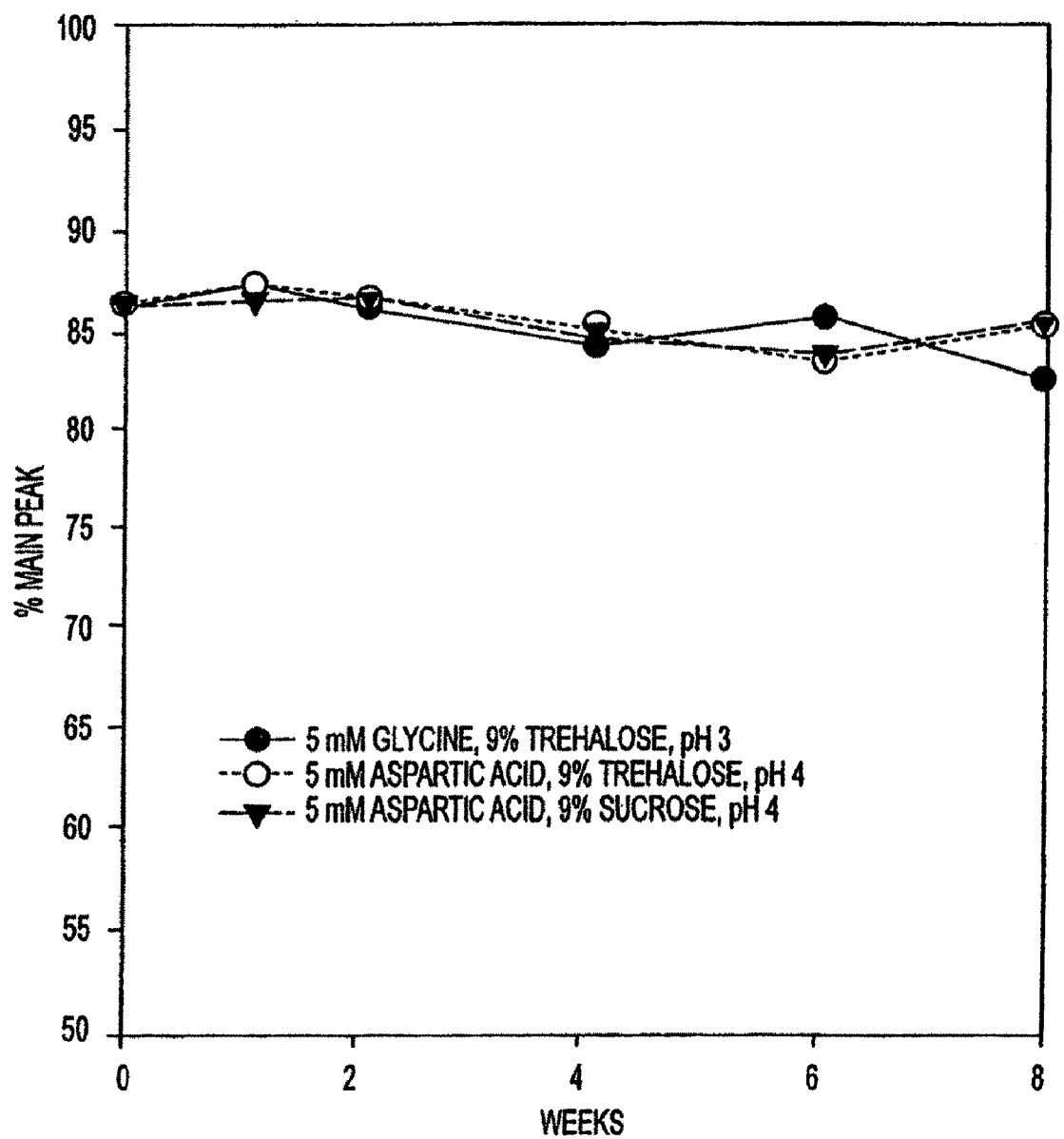
FIG. 17 shows percent of main peak IFN-β-1b in liquid formulations containing 9% trehalose or 9% sucrose following 8-weeks storage at 30° C. Percent main peak was determined by RP-HPLC analysis.

Stability of Liquid IFN-β-1b HSA-Free Formulations Under Accelerated Temperature Conditions The stability of HSA-free formulations of IFN-β-1b at pH 3.0 and pH 4.0 were also examined in the liquid state. The composition of the formulations were the same as outlined in Example 3 (9% trehalose (pH 3.0 and pH 4.0) or 9% sucrose (pH 4.0)). Again, to minimize the ionic strength of the formulations and thus minimize the amount of aggregated IFN-β-1b, the amount of buffer was kept to a minimum level (5 mM). Liquid formulations were stored at 30° C. and their stability measured over 9 weeks. The typical storage condition for liquid protein formulations is 5° C. Therefore, 30° C. storage represents accelerated temperature conditions designed to increase the rate of IFN-β-1b degradation. Results shown in FIG. 16 (concentration measurements) and FIG. 17 (reverse-phase HPLC analysis) show no detectable changes in the formulations over the 9-week study. These results indicate that in these formulations under these conditions, the IFN-β-1b is stable over the course of the study.

Example 6

Figure 18:
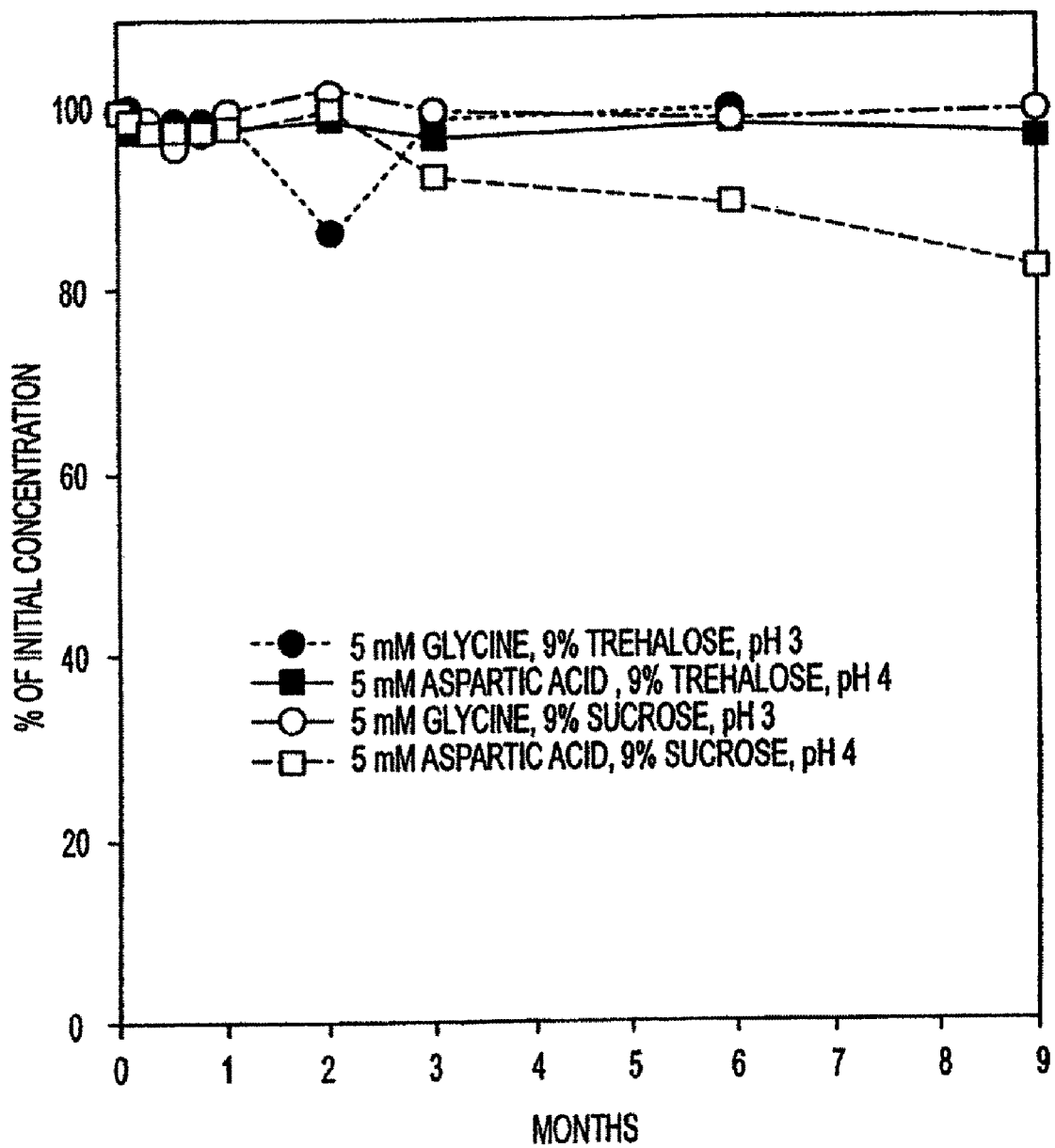
FIG. 18 shows percent of initial UN-β-1b concentration in liquid formulations containing 9% trehalose or 9% sucrose following 9-months storage in vials at 5° C. Concentration was determined by UV spectroscopy.
Figure 19:
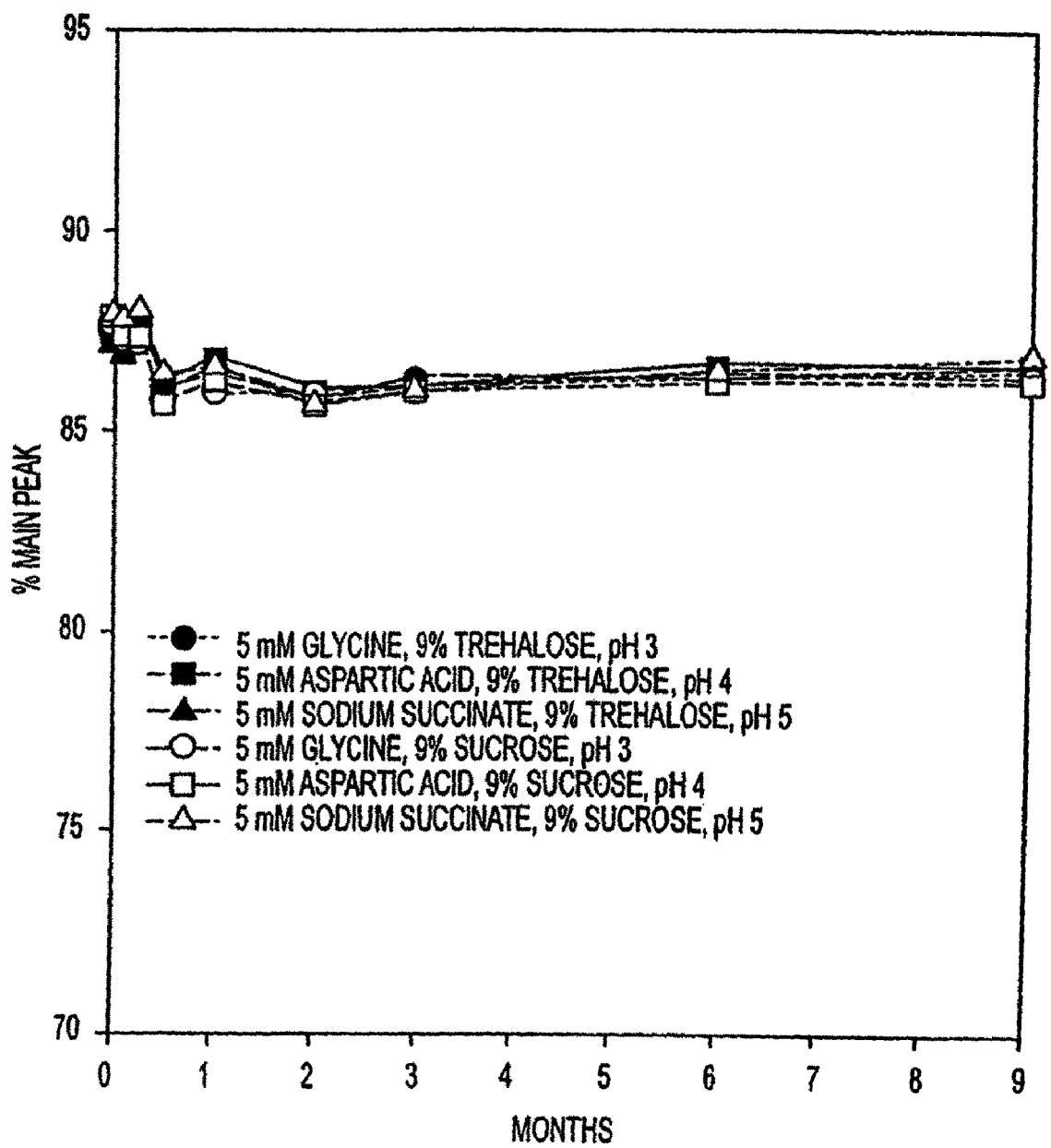
FIG. 19 shows percent main peak IFN-β-1b in liquid formulations containing 9% trehalose or 9% sucrose following 9-months storage in vials at 5° C. Percent main peak was determined by RP-HPLC analysis.

Stability of Liquid IFN-β-1b HSA Free Formulations Under Real Time Storage Conditions In this experiment, liquid formulations containing 9% trehalose (5 mM glycine, pH 3, or 5 mM aspartic acid, pH 4) or 9% sucrose (5 mM glycine, pH 3 or 5 mM aspartic acid, pH 4) were examined under real time storage conditions of 5° C. Formulations were filled into vials and their stabilities measured over 9 months. Results for concentration measurements and reverse-phase HPLC (RP-HPLC) analysis are shown in FIG. 18 and FIG. 19, respectively. These results indicate that the IFN-β-1b in these formulations is stable during the 9 months of this study.

Example 7

Figure 20:
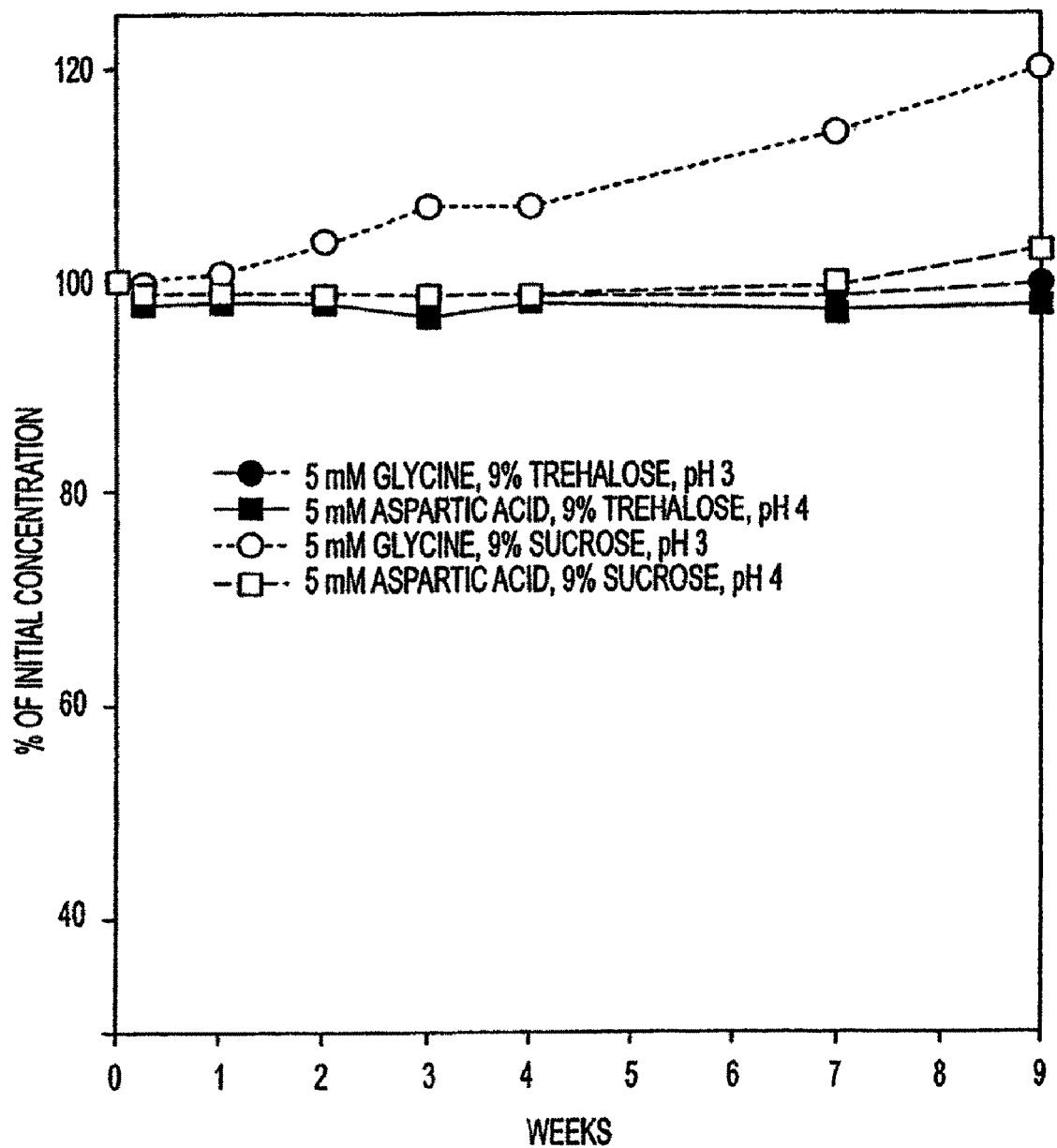
FIG. 20 shows percent of initial IFN-β-1b concentration in liquid formulations containing 9% trehalose or 9% sucrose following 9-weeks storage at 30° C. Concentration was determined by UV spectroscopy.
Figure 21:
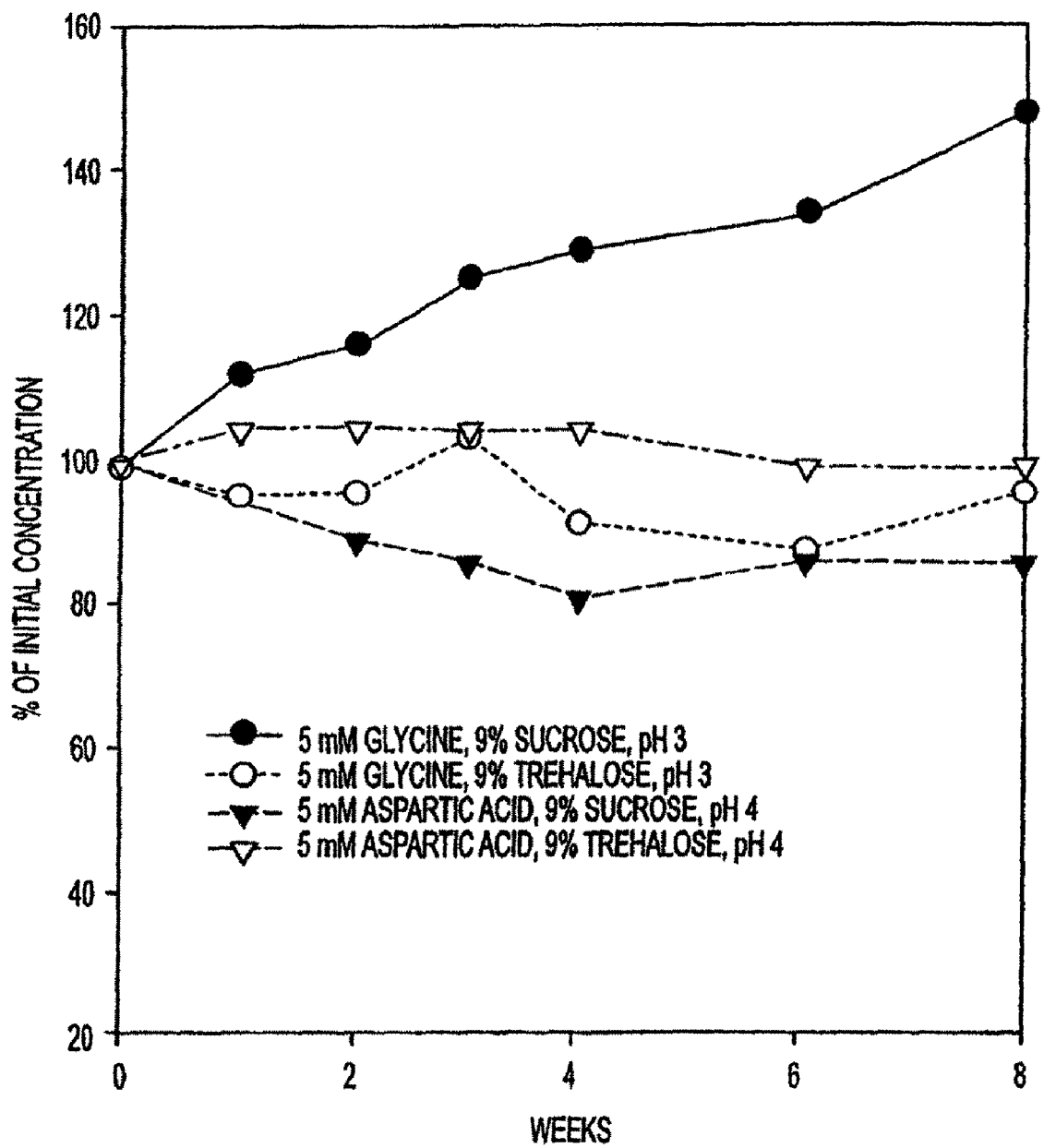
FIG. 21 shows percent of initial IFN-β-1b concentration in lyophilized formulations containing 9% trehalose or 9% sucrose following 8-weeks storage at 40° C. Concentration was determined by UV spectroscopy.

Trehalose is Preferable to Sucrose as a Non-Ionic Tonicifying Agent for IFN-β-1b Formulations In this experiment, formulations containing 9% trehalose (5 mM glycine, pH 3, or 5 mM aspartic acid, pH 4) and 9% sucrose (5 mM glycine, pH 3, or 5 mM aspartic acid, pH 4) were prepared and filled into vials as a liquid, and vials of the same formulation were lyophilized. Their stabilities were measured under accelerated temperature conditions, which are often predictive of the rank order stability of formulations of a given protein. Liquid formulations were stored at 30° C. for 9 weeks, and lyophilized formulations were stored at 40° C. for 8 weeks. Results of concentration measurements are shown in FIG. 20 (liquid) and FIG. 21 (lyophilized). These results indicate that formulations at pH 3 containing sucrose show an apparent increase in concentration. This apparent increase in concentration is due to the hydrolysis of sucrose at low pH to form reducing sugars, which results in non-enzymatic browning (i.e., maillard reaction) of the formulations. Trehalose is much more resistant to hydrolysis, and it is therefore preferred over sucrose in these formulations (see, O'Brien (1996) *Science* 61:679-682).

Example 8

Removal of SDS and Formulation of IFN-β-1b Using Guanidine Hydrochloride Precipitation Purified IFN-β-1b (1 L of 1.91 mg/ml in 0.4% SDS, 50 mM acetate buffer, pH 5.5) was stored at 5° C. During storage, some of the SDS present precipitated. 250 ml of this material (477.5 mg) was mixed with 229 g of guanidine hydrochloride (6 M, total volume 400 ml) and stirred at room temperature for 15 minutes using a magnetic stir bar. The 6 M guanidine hydrochloride/protein solution was then filtered with a Sartobran® P Capsule (0.45 μm pore size) to remove the precipitated SDS. The protein concentration as determined by UV at 280 nm was 1.02 mg/ml. The protein yield was 406 mg or 85%.

The 400 ml guanidine-hydrochloride treated material was concentrated utilizing a Millipore® Labscale® TFF diafiltration system (Millipore, Inc.) with two Pellicon® XL Biomax® 0.1 cm$^2$ 10 kD polysulfone membranes (Millipore, Inc. The volume following the concentration step was 37 ml with a protein concentration of 10.3 mg/ml for a post concentration yield of 381 mg or 93%.

Using a transfer pipette, 10 ml (103 mg) of the concentrated guanidine hydrochloride/protein solution were gradually added to 590 ml of 5 mM glycine, pH 3.2 solution. The buffer was at a rapid stir using a magnetic stir bar; the protein solution was added directly to the vortex. This 60× dilution of the 6 M guanidine hydrochloride/protein solution yielded a 0.1 M guanidine hydrochloride/protein solution at 0.17 mg/ml. This 600 ml was transferred to a 500 ml scale diafiltration unit equipped with two Pellicon® II 10kD, 0.1 m$^2$ polysulfone membranes. This solution was initially concentrated to ~400 mL to a protein concentration of 0.23 mg/ml, and subsequently diafiltered against 9 volume changes (3.6 L) of 5 mM glycine at pH 3.2. The final diafiltrate (402 ml) was measured by UV at 280 nm for a final protein concentration of 0.23 mg/ml with a 92.46 mg or 90% yield for the diafiltration step and an overall yield of 72% soluble protein for the purification process.

Example 9

Figure 22:
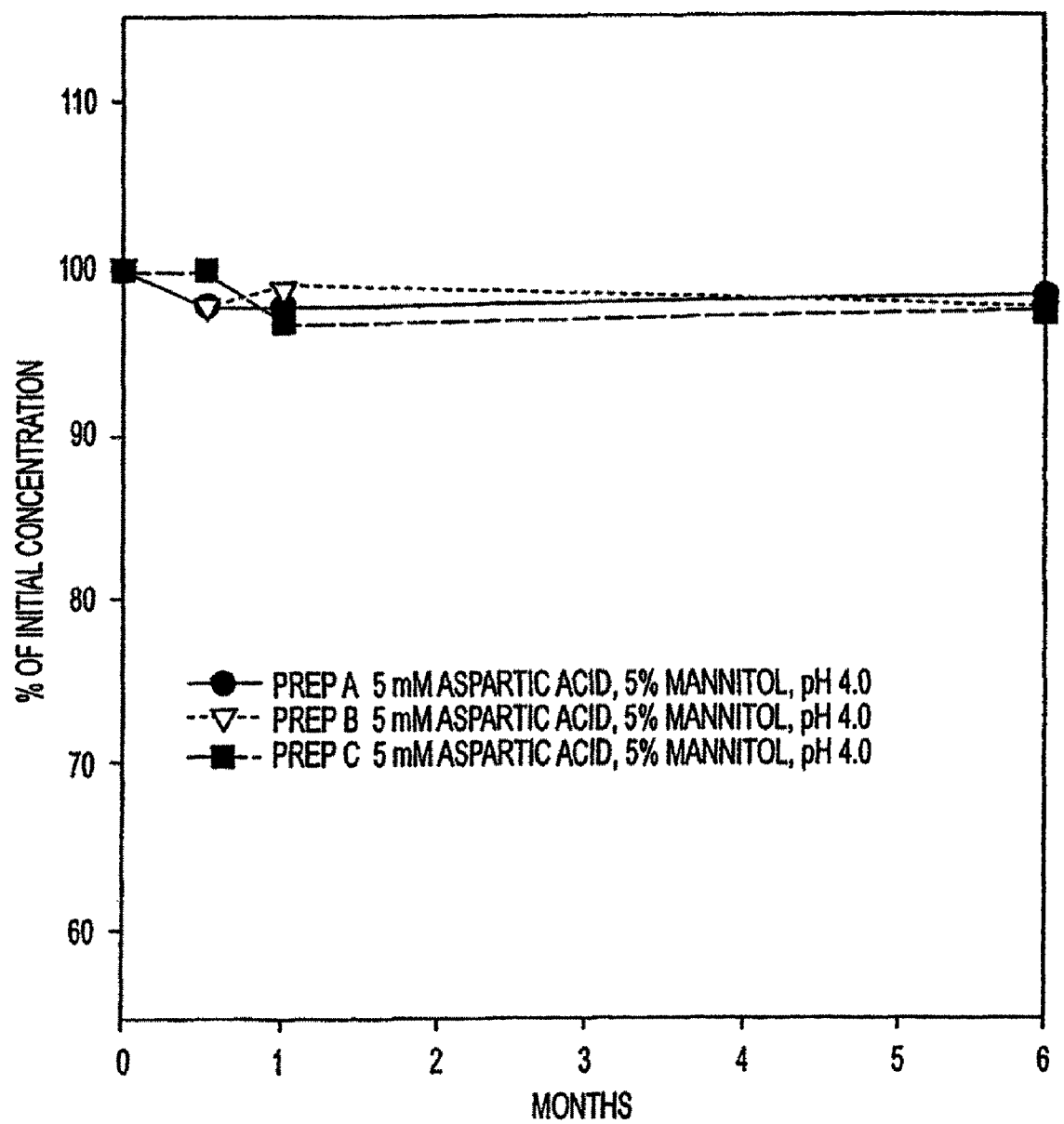
FIG. 22 shows percent of initial IFN-β-1b concentration in liquid formulations containing 5% mannitol with 6-months storage at 5° C. Concentration was determined by UV spectroscopy.
Figure 23:
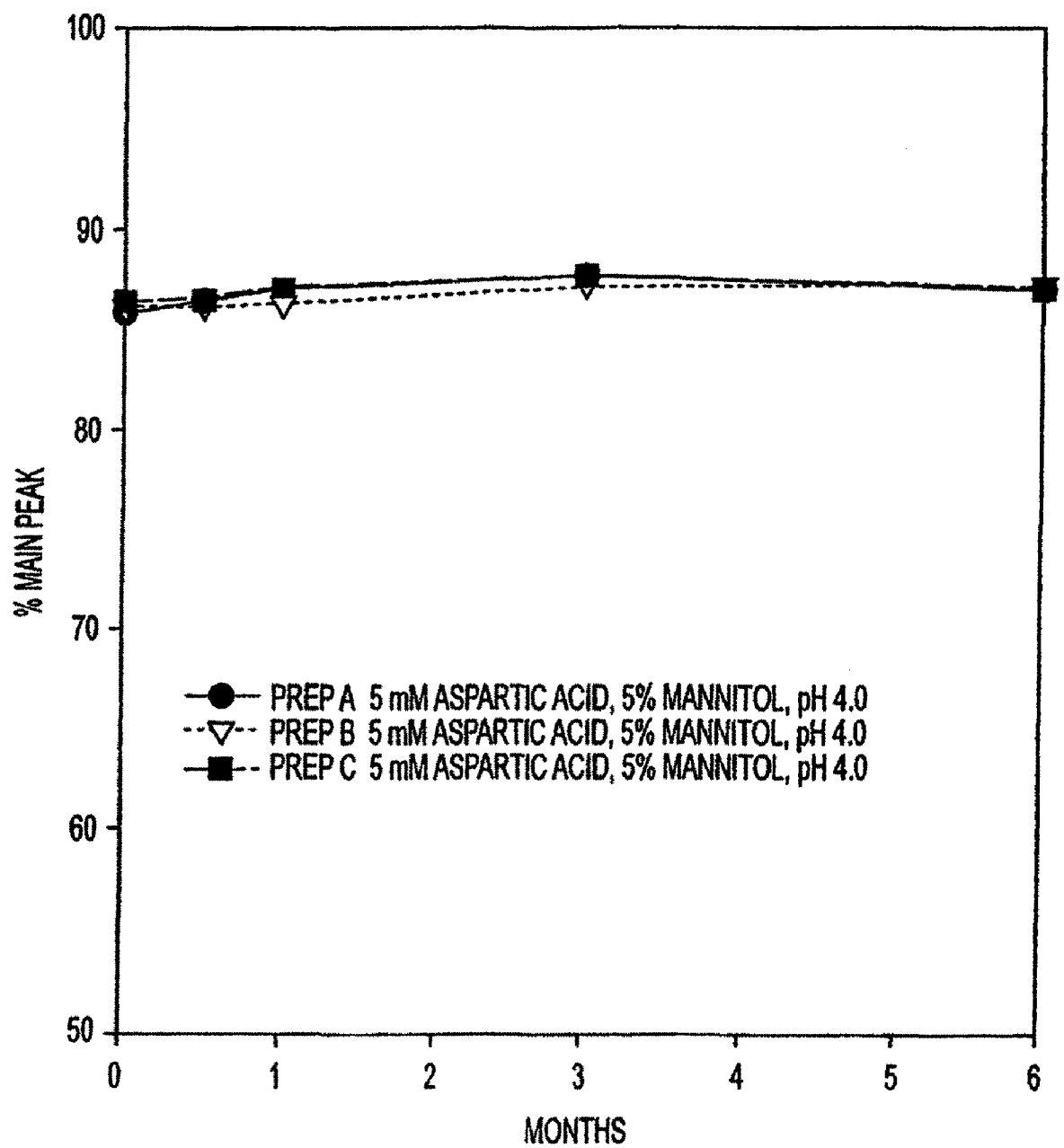
FIG. 23 shows percent of main peak IFN-β-1b in liquid formulations containing 5% mannitol with 6-months storage at 5° C. Percent of main peak was determined by RP-HPLC.

Stability of Liquid IFN-β-1b HSA Free Formulations Containing Mannitol as the Tonicifying Agent In this experiment, liquid formulations containing 5 mM aspartic acid, 5% mannitol were examined under real-time storage conditions of 5° C. Three separate preparations (designated Prep A, Prep B, and Prep C in the figures) were prepared from a single lot of HSA-free IFN-β-1b and filled into vials. The vials were stored at 5° C., and the stability of the formulations was measured over 6 months. Results for concentration measurements and reverse-phase HPLC (RP-HPLC) analysis are shown in FIG. 22 and FIG. 23, respectively. Results demonstrate that no detectable changes occur in these IFN-β-1b formulations over the 6-month study.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Subheadings in the specification document are included solely for ease of review of the document and are not intended to be a limitation on the contents of the document in any way.

Although the foregoing invention has been described in some detail by way of illustration and example for purposes of clarity of understanding, it will be obvious that certain changes and modifications may be practiced within the scope of the invention.

We claim:

1. A pharmaceutical composition that is HSA-free comprising substantially monomeric interferon-beta (IFN-β) or biologically active variant thereof in a formulation having an ionic strength that is not greater than about 20 mM and comprising a buffer at a concentration of about 2 mM to about 20 mM, where the composition has a pH of about 3.0 to about 4.5 and where the composition retains the IFN-β or biologically active variant thereof in its substantially monomeric state during storage in liquid form for at least about 6 months when stored at 2-8° C.

2. The composition of claim 1, wherein said buffer is present at a concentration of (i) about 1 mM to about 20 mM; (ii) about 1 mM to about 10 mM; (iii) about 2 mM to about 7 mM; (iv) about 2 mM to about 5 mM; or (v) about 5 mM.

3. The composition of claim 1, wherein the buffer is selected from: glycine; aspartic acid; sodium succinate; citrate; formate; acetate; glutamic acid; histidine; imidazole; and phosphate.

4. The composition of claim 3, wherein the buffer is acetate.

5. The composition of claim 1, wherein the pH is: (i) about 3.0 to about 4.0; (ii) about 3.5 to about 4.0; or (iii) about 4.0.

6. The composition of claim 5, wherein the composition has a pH of about 4.0.

7. The composition of claim 1, further comprising an amount of a non-ionic tonicifying agent sufficient to render said composition isotonic, wherein the non-ionic tonicifying agent is selected from the group consisting of trehalose, sucrose, mannitol, or a combination thereof.

8. The composition of claim 7, wherein the non-ionic tonicifying agent is mannitol at a concentration of about 5% by weight per volume.

9. The composition of claim 1, wherein said composition is an aqueous solution or an aqueous suspension.

10. The composition of claim 1, wherein the formulation does not have additional ionic species.

11. The composition of claim 1, wherein the composition includes a non-ionic surfactant.

12. The composition of claim 11, wherein the non-ionic surfactant is a: polyoxyethylene sorbitol ester, such as polysorbate 80 or polysorbate 20; or a block copolymer based on ethylene oxide and propylene oxide, such as poloxamer 188 and poloxamer 407; or a polyoxyethylene alcohol.

13. The composition of claim 1, wherein said IFN-β is the polypeptide with the amino acid sequence of mature native IFN-β or biologically active variant thereof.

14. The composition of claim 1, wherein the IFN-β is glycosylated or unglycosylated.

15. The composition of claim 14, wherein said IFN-β is unglycosylated human IFN-β (hIFN-β) or biologically active mutein thereof.

16. The composition of claim 1, wherein the IFN-β is present at a concentration of about 0.01 mg/ml to about 20.0 mg/ml.

17. The composition of claim 1, wherein the composition is stored in a prefilled, ready-to-use syringe.

18. The composition of claim 1, for use in treating multiple sclerosis.

19. The composition of claim 1, further comprising mannitol and wherein the IFN-β or biologically active variant thereof is glycosylated.

20. The composition of claim 1, further comprising mannitol at a concentration of about 4% to about 6% by weight per volume.

21. The composition of claim 1, wherein the IFN-β or biologically active variant thereof is glycosylated and the buffer is at a concentration of about 2 mM to about 10 mM.

22. The composition of claim 1, further comprising a surfactant and wherein the IFN-β or biologically active variant thereof is glycosylated.

23. The composition of claim 22, wherein said IFN β r biologically active variant thereof or biologically active variant thereof is present at a concentration of about 0.075 mg/ml to about 6.0 mg/ml.

24. The composition of claim 22, wherein the composition is formulated for subcutaneous injection.

25. The composition of claim 22, wherein the composition is formulated for treating relapsing multiple sclerosis.

26. The composition of claim 25, wherein the shelf-life is at least 12 months.

27. The composition of claim 25, wherein the shelf-life is at least 18 months.

28. The composition of claim 25, wherein the shelf-life is at least 22 months.

29. The composition of claim 1, further comprising a surfactant and wherein the IFN-β or biologically active variant thereof is present at a concentration of about 0.025 mg/ml to about 10.0 mg/ml.

30. The composition of claim 1, wherein the composition has a shelf-life of at least about 6 months when stored at 2-8° C.

31. The composition of claim 1, further comprising an amino acid.

32. The composition of claim 1, wherein the composition is in liquid form in a prefilled, ready-to-use syringe and wherein said IFN-β or biologically active variant thereof is present at a concentration of about 0.025 mg/ml to about 10.0 mg/ml.

33. The composition of claim 1, wherein the composition is in liquid form as a multidose preparation, wherein said IFN-β or biologically active variant thereof is present at a concentration of about 0.025 mg/ml to about 10.0 mg/ml.

34. A pharmaceutical composition that is HSA-free comprising substantially monomeric glycosylated interferon-beta (IFN-β) or biologically active variant thereof in a low-ionic-strength formulation, wherein said low-ionic-strength formulation is a solution that comprises buffer in a concentration of about 2 mM to about 20 mM, wherein said formulation is prepared in the absence of HSA, has a pH of about 3.0 to about 4.5, an ionic strength that is not greater than about 20 mM, and is suitable for pharmaceutical use, and wherein said IFN-β or biologically active variant thereof has 95% or more sequence identity to the amino acid sequence of SEQ ID NO: 1, and where the composition retains the IFN-β or biologically active variant thereof in its substantially monomeric state during storage in liquid form for at least about 6 months.

35. A pharmaceutical composition that is HSA-free comprising substantially monomeric glycosylated interferon-beta (IFN-β) in a low-ionic-strength formulation, wherein said low-ionic-strength formulation is a solution that comprises buffer in a concentration of about 2 mM to about 20 mM, wherein said formulation is prepared in the absence of HSA, has a pH of about 3.0 to about 4.5, an ionic strength that is not greater than about 20 mM, and is suitable for pharmaceutical use, and wherein said IFN-β has the amino acid sequence of SEQ ID NO: 1, and where the composition retains the IFN-β in its substantially monomeric state during storage in liquid form for at least about 6 months.

36. A pharmaceutical composition that is HSA-free comprising substantially monomeric glycosylated interferon-beta (IFN-β) in a low-ionic-strength formulation, wherein said low-ionic-strength formulation is a solution that comprises a buffer in a concentration of about 2 mM to about 20 mM, where the pH of said HSA-free pharmaceutical composition is about 3.0 to about 4.5, said composition further comprises mannitol, said formulation having an ionic strength that is not greater than about 20 mM, and wherein said IFN-β has the amino acid sequence of SEQ ID NO: 1 and is present at a concentration of about 0.015 mg/ml to about 12.5 mg/ml, and where the composition retains the IFN-β in its substantially monomeric state during storage in liquid form for at least about 6 months.

37. A pharmaceutical composition that is HSA-free comprising substantially monomeric interferon-beta (IFN-β) or biologically active variant thereof solubilized in a low-ionic-strength formulation having an ionic strength that is not greater than about 20 mM, wherein said low-ionic-strength formulation is a solution that comprises a buffer at a concentration of about 1 mM to about 30 mM to maintain the pH of said composition within plus or minus 0.5 units of a specified pH, and wherein the composition has a pH of 3.0 to 4.5, and where the composition retains the IFN-β or biologically active variant thereof in its substantially monomeric state during storage in liquid form for at least about 6 months.

38. The composition of any one of claims 1-18, 4-24, 25, and 29-37, further comprising a solubilizing agent or solubility enhancer.

39. The composition of any one of claims 1-18, 4-24, 25, and 29-37, wherein the IFN-β or biologically active variant thereof is recombinantly produced in a mammalian host cell.

40. A method for preparing an HSA-free pharmaceutical composition comprising substantially monomeric interferon-beta (IFN-β), said method comprising preparing said composition with a low-ionic-strength formulation, wherein said low-ionic-strength formulation is a solution that comprises a buffer in an amount sufficient to maintain the pH of said composition within plus or minus 0.5 units of a specified pH, wherein the specified pH is about 3.0 to about 5.0, said formulation having an ionic strength not greater than 40 mM, and incorporating said IFN-β or biologically active variant thereof into said composition.

41. The method of claim 40, wherein said buffer is present at a concentration of (i) about 1 mM to about 30 mM; or (ii) about 2 mM to about 5 mM.

42. A pharmaceutical composition produced according to the method of claim 40.

43. A method for treating relapsing multiple sclerosis in a human subject, comprising administering to the subject by subcutaneous injection the composition of claim 25.

* * * * *